(12) United States Patent
Leduc et al.

(10) Patent No.: US 6,416,770 B1
(45) Date of Patent: Jul. 9, 2002

(54) USE OF HETEROCYCLIC QUATERNARY POLYAMMONIUM POLYMERS AS PROTECTIVE AGENT FOR KERATIN FIBRES AND COSMETIC COMPOSITIONS

(75) Inventors: Madeleine Leduc, Paris; Hervé Richard, Villepinte; Alain Lagrange, Coupvray, all of (FR)

(73) Assignee: L'Oréal S.A., Paris (FR)

( * ) Notice: Subject to any disclaimer, the term of this patent is extended or adjusted under 35 U.S.C. 154(b) by 0 days.

(21) Appl. No.: 09/601,020

(22) PCT Filed: Jan. 18, 1999

(86) PCT No.: PCT/FR99/00085

§ 371 (c)(1),
(2), (4) Date: Sep. 21, 2000

(87) PCT Pub. No.: WO99/37276

PCT Pub. Date: Jul. 29, 1999

(30) Foreign Application Priority Data

Jan. 26, 1998 (FR) ............................................ 98 00793

(51) Int. Cl.[7] .......................... A61K 6/00; A61K 7/075; C08G 18/28; C08G 69/26; C07D 403/02
(52) U.S. Cl. .......................... 424/401; 528/73; 528/350; 548/312.7; 510/126
(58) Field of Search .......................... 424/401; 528/350, 528/73, 312.7; 510/126

(56) References Cited

U.S. PATENT DOCUMENTS

| | | | |
|---|---|---|---|
| 3,852,259 A | * 12/1974 | Bracke | 260/94.1 |
| 4,217,914 A | 8/1980 | Jacquet et al. | |
| 4,349,532 A | 9/1982 | Vanlerberghe et al. | |
| 4,533,714 A | 8/1985 | Sebag et al. | |
| 4,749,732 A | 6/1988 | Kohl et al. | |
| 4,792,383 A | * 12/1988 | Willis | 205/307 |
| 5,081,213 A | * 1/1992 | Carlson | 528/73 |
| 5,120,825 A | * 6/1992 | Vora et al. | 528/350 |
| 5,618,523 A | 4/1997 | Zysman et al. | |
| 5,661,118 A | * 8/1997 | Cauwet et al. | 510/126 |
| 5,708,151 A | 1/1998 | Möckli | |
| 6,096,899 A | * 8/2000 | Rasmussen et al. | 548/312.7 |
| 6,240,929 B1 | * 6/2001 | Richard et al. | 132/202 |

FOREIGN PATENT DOCUMENTS

| | | |
|---|---|---|
| EP | 0 227 994 | 7/1987 |
| EP | 0 295 780 | 1/1988 |
| EP | 0 714 954 | 6/1996 |
| FR | 1 530 369 | 6/1968 |
| FR | 2 270 846 | 12/1975 |
| FR | 2 413 907 | 8/1979 |
| FR | 2 535 730 | 5/1984 |
| FR | 2 673 179 | 8/1992 |
| FR | 2 740 031 | 4/1997 |
| GB | 2 197 352 | 5/1988 |
| JP | 62-167771 | * 7/1987 |
| WO | WO 92/05764 | 4/1992 |
| WO | WO 94/07844 | 4/1994 |
| WO | WO 95/01772 | 1/1995 |
| WO | WO 95/15144 | 6/1995 |

OTHER PUBLICATIONS

Bol, US Statutory Invention Registration H385, Dec. 1, 1987.*
Patent Abstracts of Japan, vol. 12, No. 11, Jan. 13, 1988 (JP 62 167771).
J. Torres, "Synthesis and Physiocochemical Studies on 1,2–Bisazolylethanes", Journal of Heterocyclic Chemistry, vol. 25, No. 3, May–Jun. 1988, pp. 771–782.
Ying–Hung So, "Novel Thermoset Polyimidazole Amides", Macromolecules, vol. 25, No. 2, 1992, pp. 516–520.
Cheng He Zhou et al., "A Convenient and Efficient Synthesis of Bis–Imidazoles", Chinese Chemical Letters, vol. 7, No. 4, 1996, pp. 321–324.
Kristi J. Robson et al., "6–Hydroxy–4–sphingenine in Human Epidermal Ceramides", Journal of Lipid Research, vol. 35, No. 11, 1994, pp. 2060–2068.

* cited by examiner

Primary Examiner—Michael G. Hartley
Assistant Examiner—Michael A. Willis
(74) Attorney, Agent, or Firm—Finnegan, Henderson, Farabow, Garrett & Dunner, L.L.P.

(57) ABSTRACT

The invention relates to the use of heterocyclic quaternary polyammonium polymers as protective agent for keratin fibres, to cosmetic compositions using them and to method for treating hair with the aid of these polymers.

230 Claims, No Drawings

USE OF HETEROCYCLIC QUATERNARY POLYAMMONIUM POLYMERS AS PROTECTIVE AGENT FOR KERATIN FIBRES AND COSMETIC COMPOSITIONS

This application is a 371 of PCT/FR99/00085 submitted Jan. 18, 1999.

The present invention relates to the use as protective agent for keratinous fibres of poly(heterocyclic quaternary ammonium) polymers, to cosmetic compositions employing them and to hair treatment processes in which these polymers are used.

Provision has already been made to use polymers comprising quaternary ammonium groups as hair conditioning agents. Such compositions are disclosed in particular in the French patents of the Applicant Company Nos. 2,270,846, 2,307,271 and 2,413,907.

Cationic polymers exhibit a high affinity for keratinous fibres, such as the hair, due to the interaction of the cationic groups with the anionic groups of the individual hair.

The deposition of these polymers on the hair becomes easier as the latter becomes more sensitized and their affinity for the hair is often such that they withstand removal by shampooing or by brushing.

However, it has been found that, while the use of such cationic polymers exhibits numerous advantages in so far as they facilitate disentangling of the hair and as they confer qualities of liveliness and a glossy appearance thereon, due to their affinity for keratin, these polymers have a tendency to accumulate on the hair following repeated applications.

Cationic polymers comprising quaternary groups furthermore often exhibit the disadvantage of not being very compatible with anionic surface-active agents, which reduces the possibilities of use and requires them to be used in two-step treatments, before or after shampooing.

The Applicant Company has discovered that some poly(quaternary ammonium) polymers, which do not exhibit the abovementioned disadvantages, comprising at least unsaturated quaternary heterocycles, are particularly advantageous in hair treatment.

The Applicant Company has discovered in particular that the use of these polymers makes it possible to protect the hair both with regard to attacks due in particular to the sun, to bad weather or to perspiration and with regard to those resulting from hair treatment, such as, for example, bleachings, permanent waves or dyeings.

It has been found that keratinous fibres have a tendency to be rendered brittle when they are subjected to these treatments; the hair becomes dry, dull and rough, and difficult to disentangle and to style.

The protective agents of the invention are of use in particular in any cosmetic process comprising at least one stage during which the keratinous fibres are liable to be exposed to various attacks and thus make it possible to avoid the abovementioned disadvantages.

These protective agents can be applied to the keratinous fibres during, prior to or subsequent to this stage during which the keratinous fibres are subjected to attacks.

The protective agents of the present invention are preferably used in a process during which at least one application of an alkaline composition to the keratinous fibres takes place.

A subject-matter of the invention is thus the use as protective agent of heterocyclic polyquaternary polymers.

Another subject-matter of the invention is cosmetic compositions employing them and in particular compositions intended for permanent shaping of keratinous fibres, bleaching compositions and dyeing compositions, preferably oxidation dyeing compositions.

A further subject-matter of the invention is a hair treatment process employing these compositions.

Other subject-matters of the present application will emerge on reading the description and examples which follow.

The polymers used as protective agent for keratinous fibres are basically composed of repeat units of formula (I):

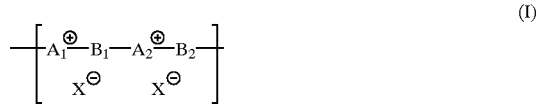

in which:

$A_1^p$ and $A_2^p$, which are identical or different, denote:

a) an unsaturated quaternary heterocycle of formula (II):

in which:

E, G, L and J, which are identical or different, denote a carbon, oxygen, sulphur or nitrogen atom, at least one denoting a nitrogen atom;

E, G, L and J can be substituted, when one or more of these atoms denote a carbon atom, by one or more halogen atoms, hydroxyl, nitro, cyano, mercapto or carboxyl groups, an alkyl, monohydroxyalkyl, polyhydroxyalkyl, thioalkyl, cyanoalkyl, alkoxy, acyl or acetyloxy group, a substituted or unsubstituted cycloalkyl, substituted or unsubstituted aryl or substituted or unsubstituted alkylaryl group, or —$NHR_N$ groups in which $R_N$ denotes an acetyl or ureido group.

When E, G, L or J denotes a third nitrogen atom, the latter can be substituted by a hydrogen or an alkyl, monohydroxyalkyl, polyhydroxyalkyl, substituted or unsubstituted aryl or substituted or unsubstituted alkylaryl radical.

The substituents of two of the E, G, L and J atoms can also form, jointly with the atoms to which they are attached, a substituted or unsubstituted 5- to 7-membered aromatic ring; or b) a quaternary ammonium of formula (III)

in which:

$R_1$ and $R_2$, which are identical or different, denote a carboxyl group, an alkyl, polyhydroxyalkyl, thioalkyl, cyanoalkyl, alkoxy, acyl or acetyloxy group, a substituted or unsubstituted cycloalkyl, substituted or unsubstituted aryl or substituted or unsubstituted alkylaryl group or an —$NHR_N$ group in which $R_N$ denotes an acetyl or ureido group;

$R_1$ and $R_2$ can also form, jointly with the nitrogen atom to which they are attached, a saturated 5- to 7-membered carbonaceous ring;

and in which at least one of the $A_1^p$ or $A_2^p$ groups denotes an unsaturated quaternary heterocycle of formula (II).

$B_1$ and $B_2$, which are identical or different, denote a hydrocarbonaceous group which can comprise, bonded to or inserted in the main chain, one or more substituted or unsubstituted aromatic rings, one or more oxygen, sulphur or nitrogen atoms, or one or more —SO—, —SO$_2$—, —SO$_3$H, amino, alkylamino, hydroxyl, quaternary ammonium or ureido groups.

$X^\ominus$ represents an anion derived from an organic or inorganic acid.

The polymers of the present invention have a mass-average molecular weight preferably of between 1000 and 20,000, measured by gel permeation chromatography using polyethylene glycol as reference.

In the context of the present invention:

The halogen atoms preferably denote a fluorine, chlorine, bromine or iodine atom.

The alkyl, monohydroxyalkyl or polyhydroxyalkyl radicals and the hydrocarbonaceous groups can be linear or branched.

The alkyl groups denote in particular groups of 1 to 20 carbon atoms, such as, for example, the methyl, ethyl, propyl, isopropyl, n-propyl, butyl, n-butyl, tert-butyl, pentyl, n-pentyl, isopentyl, n-hexyl, isohexyl, heptyl, octyl, nonyl, decyl, undecyl, dodecyl and pentadecyl groups. The alkyl groups preferably denote a group of 1 to 6 carbon atoms.

Mention may be made, among the hydrocarbonaceous groups, of polymethylene groups of 1 to 20 carbon atoms.

The hydrocarbonaceous groups preferably denote polymethylene groups of 2 to 8 carbon atoms.

The hydrocarbonaceous groups can comprise, bonded to or inserted in the main chain, one or more aromatic rings, one or more oxygen, sulphur or nitrogen atoms, or one or more —SO—, —SO$_2$—, —SO$_3$H, amino, alkylamino, hydroxyl, quaternary ammonium or ureido groups.

Mention may in particular be made, among the monohydroxyalkyl groups, of hydroxymethyl, hydroxyethyl, hydroxypropyl and hydroxybutyl groups.

Mention may be made, among the Apolyhydroxyalkyl radicals, of, for example, dihydroxyethyl, dihydroxypropyl, trihydroxypropyl and dihydroxybutyl radicals.

The thioalkyl radicals denote an —R—SH group, R representing an alkyl group as defined above.

The cyanoalkyl radicals denote an —R—C≡N group, R representing an alkyl group as defined above.

The alkoxy groups denote an —O—R group, R representing an alkyl group as defined above.

The acyl groups denote an —OC—R group, R representing an alkyl group as defined above.

The acetyloxy groups denote an —O—CO—R group, R representing an alkyl group as defined above.

Mention may in particular be made, among the cycloalkyl radicals, of cyclohexyl and cyclopentyl.

Mention may in particular be made, among the aryl radicals, of phenyl or naphthyl groups.

Mention may in particular be made, among the alkylaryl groups, of the benzyl, phenethyl or naphthylmethyl group.

Mention may be made, among the 5- to 7-membered aromatic rings, of, for example, the abovementioned aryl or alkylaryl rings. The preferred aromatic rings are phenyl, pyrimidine, pyridine, pyrrole and pyrazole rings.

In the context of the present invention, the cycloalkyl radicals and the aromatic rings can be substituted by a halogen atom or a hydroxyl, amino or $C_1$–$C_6$ alkyl or hydroxyalkyl group.

$X^\ominus$ represents in particular an anion derived from a halogen, such as chlorine, bromine, fluorine or iodine, an anion derived from inorganic acids, such as phosphoric acid or sulphuric acid, or an anion derived from an organic sulphonic or carboxylic acid, in particular an alkanoic acid having from 1 to 12 carbon atoms, such as acetic acid, a phenylalkanoic acid, such as phenylacetic acid, benzoic acid, citric acid or para-toluenesulphonic acid. $X^\ominus$ preferably represents an anion derived from a halide and more preferably $X^\ominus$ represents a chloride or bromide anion.

$A_1$ and/or $A_2$ preferably represents a heterocycle of formula (II) comprising 2 nitrogen atoms and 3 carbon atoms.

In a preferred embodiment of the present invention, at least one of the $A_1$l or $A_2^p$ groups denotes a quaternary imidazole group of formula (IV):

(IV)

in which:

$R_3$, $R_4$ and $R_5$, which are identical or different, denote a hydrogen or halogen atom, a hydroxyl, nitro, cyano, mercapto or carboxyl group, an alkyl, monohydroxyalkyl, polyhydroxyalkyl, thioalkyl, cyanoalkyl, alkoxy, acyl or acetyloxy group, a cycloalkyl, aryl or alkylaryl group or an —NHR$_N$ group in which R$_N$ denotes an acetyl or ureido group; the $R_4$ and $R_5$ radicals can also form, jointly with the atoms to which they are attached, a 5- to 7-membered aromatic ring.

In another embodiment of the present invention, at least one of the $A_1^p$ or $A_2^p$ groups denotes a quaternary pyrazole group of formula (V):

(V)

in which:

$R_6$, $R_7$ and $R_8$, which are identical or different, denote a hydrogen or halogen atom, a hydroxyl, nitro, cyano, mercapto or carboxyl group, an alkyl, monohydroxyalkyl, polyhydroxyalkyl, thioalkyl, cyanoalkyl, alkoxy, acyl or acetyloxy group, a cycloalkyl, aryl or alkylaryl group or an —NHR$_N$ group in which R$_N$ denotes an acetyl or ureido group; two of the $R_6$, $R_7$ or $R_8$ radicals can also form, jointly with the atoms to which they are attached, a 5- to 7-membered aromatic ring.

In another preferred embodiment of the present invention, the $A_1^p$ and $A_2^p$ groups simultaneously denote a quaternary imidazole group of formula (IV) in which $R_3$, $R_4$ and $R_5$, which are identical or different, denote a hydrogen atom, a hydroxyl, nitro, cyano, mercapto or carboxyl group or an alkyl, monohydroxyalkyl or polyhydroxyalkyl group; the $R_4$ and $R_5$ radicals can also form, jointly with the atoms to which they are attached, a 5- to 7-membered aromatic ring.

In another particularly preferred form of the present invention, the $A_1^p$ and $A_2^p$ groups simultaneously denote a quaternary imidazole group of formula (IV) in which $R_3$, $R_4$ and $R_5$, which are identical or different, denote a hydrogen atom or a $C_1$ to $C_6$ alkyl group and the $R_4$ and $R_5$ radicals can form, jointly with the atoms to which they are attached, a phenyl ring.

In another preferred embodiment of the present invention, $A_1^P$ represents a quaternary ammonium of formula (III) in which $R_1$ and $R_2$, which are identical or different, denote a hydrogen atom or a $C_1$ to $C_6$ alkyl group or form, jointly with the nitrogen, a 6-membered group and $A_2^P$ denotes a quaternary imidazole group of formula (IV) in which $R_3$, $R_4$ and $R_5$, which are identical or different, denote a hydrogen atom or a $C_1$–$C_6$ alkyl.

In a preferred embodiment of the invention, at least one of the $B_1$ or $B_2$ groups denotes a group of formula (VI)

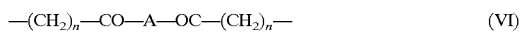  (VI)

in which:
n denotes an integer from 1 to 10 and preferably an integer from 1 to 6,
A denotes:
  (a) a glycol residue of formula:

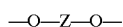

in which Z denotes a hydrocarbonaceous group or a group corresponding to the formulae:

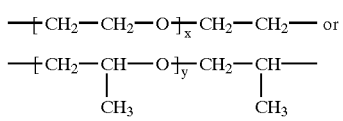

in which x and y denote any number from 1 to 4; or
  (b) a bis(secondary amine) residue, such as a piperazine derivative; or
  (c) a bis(primary amine) residue of formula:

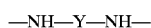

in which Y denotes a hydrocarbonaceous group or a radical

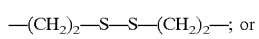; or (d) a ureylene group, that is to say a group of formula —NH—CO—NH—.

In a preferred embodiment, $B_1$ and $B_2$, which are identical or different, denote a polymethylene group which can comprise one or more oxygen atoms or one or more aromatic rings.

In a particularly preferred embodiment, $B_1$ and $B_2$, which are identical or different, denote a group of formula:

n denoting an integer from 1 to 6, or

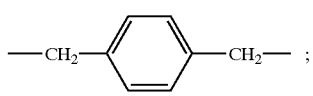

or

Preferably, in the abovementioned polymers, $X^\ominus$ represents a halide.

Some polymers used hereinabove are novel per se and constitute, as such, another subject-matter of the invention.

One family of these novel polymers is composed of the polymers based on repeat units of formula (VII):

  (VII)

in which:
$A_1^P$ denotes an unsaturated quaternary heterocycle of formula (II) as defined hereinabove and $A_2^P$ denotes a quaternary ammonium of formula (III); $B_1$, $B_2$, $X^\ominus$ and the formulae (II) and (III) being as defined hereinabove and at least one of the $B_1$ or $B_2$ groups being other than —$CH_2$—CHOH—$CH_2$—.

In the formula (VII), the unsaturated quaternary heterocycles of formula (II), the quaternary imidazole groups of formula (IV) as defined hereinabove and the quaternary pyrazole groups of formula (V) as defined hereinabove are preferred.

One family of novel polymers is basically composed of repeat units of formula (VIII):

  (VIII)

in which
$A_1^P$ denotes a quaternary imidazole group of formula (IV) as defined hereinabove and $A_2^P$ denotes a quaternary pyrazole group of formula (V) as defined hereinabove; $B_1$, $B_2$ and $X^\ominus$ being as defined hereinabove.

Another family of novel polymers is represented by the polymers basically composed of repeat units of formula (IX):

  (IX)

in which $A_1^P$ is as defined in the formula (I) and in which $A_2^P$ denotes a quaternary imidazole group of formula (IV) in which $R_4$ and $R_5$, which are identical or different, are as defined in the abovementioned formula (IV) and $R_3$ denotes a cycloalkyl, aryl or alkylaryl group and preferably a phenyl group; $B_1$, $B_2$ and $X^\ominus$ being as defined hereinabove.

Among the novel compounds (IX), those in which $A_1^P$ denotes a quaternary imidazole of formula (IV), and more particularly when the $R_3$ group of (IV) denotes a phenyl, are particularly preferred.

Among the preferred novel compounds (VII), (VIII) and (IX), $B_1$ and/or $B_2$ preferably denotes a group of formula (VI):

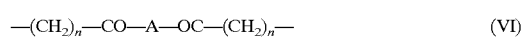  (VI)

in which:
n denotes an integer from 1 to 10;
A denotes:
  (a) a glycol residue of formula:

in which Z denotes a hydrocarbonaceous group or a group corresponding to the formulae:

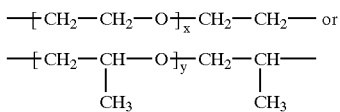

which x and y denote any number from 1 to 4; or
(b) a bis(secondary amine) residue; or
(c) a bis(primary amine) residue of formula:

—NH—Y—NH— in which Y denotes a hydrocarbonaceous group or the radical

(d) a ureylene group,
and more particularly —$(CH_2)_n$—, n denoting an integer from 1 to 6; or

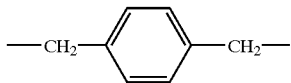

and at least one of the $B_1$ or $B_2$ groups being other than —$CH_2$—CROH—$CH_2$—, with R=H or alkyl, and the $B_1$ and $B_2$ groups being other than the group:

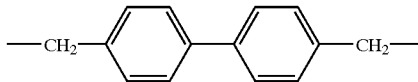

The synthesis of the compounds of the present invention is carried out in two stages. The first stage consists in synthesizing the diamine and then the second stage consists of the quaternization of the diamine in the presence of a dihalide or of a disulphonate.

The synthesis of a diamine is carried out by the reaction of the corresponding diazole with a dihalide or a disulphonate in a solvent, in the presence of a base, at a temperature between room temperature and the reflux temperature.

These solvents can be water, aromatic solvents, such as benzene or toluene, dimethyl sulphoxide, tetrahydrofuran or dimethylformamide.

These solvents can also be used as a mixture.

The bases can be hydroxides, such as sodium hydroxide or potassium hydroxide, or amides, carbonates or hydrides.

This synthesis can also take place under phase transfer conditions by the addition of a phase transfer agent.

Syntheses are described in particular in the documents J. Elguero et al., Journal of Heterocyclic Chemistry, 25, 771–782 (1988), Yin-hung So, Macromolecules, 25, 516–520 (1992) and R. G. Xie et al., Chinese Chemical Letters, 7, 321–324 (1996).

The quaternization with a dihalide or a disulphonate is carried out in a solvent at a temperature between room temperature and the reflux temperature. The solvents can be chosen from water, alcohols, aromatic solvents, such as benzene or toluene, dimethyl sulphoxide, tetrahydrofuran or dimethylformamide. These solvents can also be used as a mixture. They are preferably chosen from water, alcohols and aqueous/alcoholic mixtures.

The unsaturated heterocyclic quaternary polymers used in accordance with the invention for the protection of the hair are used in particular in compositions used for the permanent deformation of the hair, for dyeing or for bleaching which constitute another subject-matter of the invention.

The commonest technique for obtaining a permanent deformation of the hair consists, in a first step, in applying a composition comprising a reducing agent to the keratinous fibres and then, in a second step, in applying an oxidizing composition to the hair, which has been placed under tension beforehand with curlers or other means, so as to ultimately give the hair the desired shape.

The protective agents of the present invention can be present in the reducing and/or oxidizing composition.

The reducing compositions in accordance with the invention comprise, in a medium appropriate for the permanent deformation of the hair, at least one reducing agent capable of breaking the disulphide bonds (—S—S—) in the individual hairs and at least one unsaturated heterocyclic quaternary polymer as defined hereinabove.

The reducing agents are generally chosen from sulphites, bisulphites or thiols.

Mention may be made, among the preferred reducing agents, of cysteine, cysteamine and their derivatives, such as their cosmetically acceptable salts, for example the hydrochlorides, hydrobromides, citrates, acetates or sulphates, or thiolactic acid, thioglycolic acid and their esters, in particular glyceryl thioglycolate.

The reducing agents are present in proportions which are sufficient to reduce the disulphide bonds of the keratin, preferably of between 1 and 25% and in particular between 1 and 10% by weight.

The protective agents of the present invention can be present in proportions of between 0.01% and 10% by weight of the reducing composition and preferably between 1% and 5%.

The pH of the reducing compositions is adjusted so as to obtain a pH of between 6.5 and 11.5.

The alkaline agents are preferably chosen from monoethanolamine, diethanolamine, triethanolamine, isopropylamine, 2-methylamino-1-propanol, 1,3-propanediamine, an alkali metal or ammonium carbonate or bicarbonate, aqueous ammonia, an organic carbonate, such as guanidine carbonate, or an alkaline hydroxide, used alone or as a mixture.

This reducing composition can also comprise nonionic, anionic, cationic or amphoteric surface-active agents commonly used in such compositions. Mention may be made, among these, of alkyl sulphates, alkylbenzenesulphonates, alkyl ether sulphates, alkylsulphonates, quaternary ammonium salts, alkyl betaines, oxyethylenated alkylphenols, alkylpolyglucosides, fatty acid alkanolamides, oxyethylenated fatty acid esters and nonionic surfactants from the family of the hydroxypropyl ethers.

These surface-active agents are generally used in maximum proportions of 30% and preferably of between 0.5 and 10% by weight with respect to the total weight of the composition.

These compositions can also comprise thickening agents, such as guar gum, tara gum or spruce flour.

These compositions can also comprise treating agents, such as volatile or non-volatile, linear or cyclic silicones or their mixtures. Mention may be made, among the silicones, of polydimethylsiloxanes, quaternized polyorganosiloxanes as disclosed in FR-A-2,535,730, polyorganosiloxanes comprising an aminoalkyl group which are modified by alkoxycarbonylalkyl groups as disclosed in the U.S. Pat. No.

4,749,732, polyorganosiloxanes, such as polydimethylsiloxane-polyoxyalkyl copolymers, such as dimethicone copolyol, a polydimethylsiloxane comprising end stearoxy groups (stearoxydimethicone), a polydimethylsiloxane-dialkylammonium acetate copolymer or a polydimethylsiloxane-poly(alkyl betaine) copolymer disclosed in GB-A-2,197,352, polysiloxanes organomodified by mercapto or mercaptoalkyl groups as disclosed in FR-B-1,530,369 and EP-A-0,295,780, and silanes, such as stearoxytrimethylsilane.

Other ingredients which can be used in the reducing compositions comprising the protective agents of the invention are chosen from waxes, polymers chosen from cosmetically acceptable anionic, cationic (other than those of the invention), nonionic or amphoteric polymers, swelling and penetrating agents which make it possible to reinforce the effectiveness of the reducing agent, such as dimethylisosorbitol, urea and its derivatives, pyrrolidone, n-alkylpyrrolidones, thiamorpholinone, alkylene glycol or dialkylene glycol alkyl ethers, such as, for example, propylene glycol monomethyl ether or dipropylene glycol monomethyl ether, $C_3$–$C_6$ alkanediols, such as 1,2-propanediol, or 2-imidazolidinone, and other compounds, such as fatty alcohols, lanolin derivatives, ceramides, in particular ceramides themselves, glycoceramides or pseudoceramides disclosed in particular in FR-A-95 12399 and in Downing, Journal of Lipid Research, Vol. 35, p. 2060, 1994, or in FR-A-2,673,179, EP-A-0,227,994, WO-94/07844 and WO-92/05764, active ingredients, such as pantothenic acid or panthenol, agents for combating hair loss, antidandruff agents, suspending agents, sequestering agents, opacifying agents, dyes, silicone-comprising or non-silicone-comprising sunscreens, fragrances and preservatives.

The protective agents defined hereinabove can also be present in oxidizing compositions used during the permanent shaping of keratinous fibres. Another subject-matter of the invention is thus an oxidizing composition for the permanent shaping of keratinous fibres comprising, in a medium appropriate for permanent waving, an oxidizing agent and a polymer as defined hereinabove.

The oxidizing agents can be chosen from aqueous hydrogen peroxide solution, urea hydrogen peroxide, bromates, such as alkaline bromates, persalts or a mixture of alkaline bromates and of a persalt.

When the oxidizing agent is composed of aqueous hydrogen peroxide solution, it is present in proportions of between 1 and 10 volumes and preferably of the order of 8 volumes.

When bromates are used, the concentration of alkaline bromates is from 1 to 12% and that of persalts from 0.1 to 15% by weight with respect to the total weight of the oxidizing composition.

The protective agents of the present invention can be present in proportions of between 0.01% and 10% by weight of the oxidizing composition and preferably between 1% and 5% by weight.

The pH of these compositions is usually between 2 and 9 and preferably between 3 and 8; it is preferably acidic.

When aqueous hydrogen peroxide solution is used, it can be stabilized with phenacetin, acetaniline, mono- and trisodium phosphates or 8-hydroxyquinoline sulphates.

Another subject-matter of the invention is a process for the permanent shaping of keratinous fibres and in particular of the hair, essentially characterized in that:
  a composition which reduces keratin is applied to the keratinous fibres, preferably wet keratinous fibres, the reducing composition being applied to the shaped fibres, after a setting time sufficient to reduce the keratin, an oxidizing composition is applied, after a setting time sufficient to fix the fibres, shaped and reduced in the first stage, in a permanent shape, rinsing is carried out, preferably with water; the reducing composition and/or the oxidizing composition being as defined hereinabove.

The hair is shaped by various means, such as rollers, clips, hair grips or simply by hand.

Another subject-matter of the present invention is a composition for the direct dyeing of keratinous fibres and in particular of human keratinous fibres, such as the hair, comprising, in a medium appropriate for dyeing, at least one polymer as defined hereinabove and at least one direct dye.

Mention may be made, among direct dyes conventionally used, of nitrobenzene dyes, such as nitrophenylenediamines, nitrodiphenylamines, nitroanilines, nitrophenol ethers or nitrophenols, nitropyridines, anthraquinone, mono- or diazo, triarylmethane, azine, acridine and xanthene dyes or metalliferous dyes.

The direct dyes more particularly preferred according to the invention are chosen from the following:
i) nitrobenzene dyes of following formula (A):

(A)

in which $R_3$ denotes an $NH_2$ radical, an amino radical monosubstituted by an alkyl, monohydroxyalkyl, polyhydroxyalkyl or aminoalkyl radical or an amino radical disubstituted by identical or different alkyl, monohydroxyalkyl, polyhydroxyalkyl or aminoalkyl radicals, $R_4$ denotes hydrogen, hydroxyl, alcoxy, monohydroxyalkyloxy, polyhydroxyalkyloxy or the same meanings denoted hereinabove for $R_3$, with the exception of the disubstituted amino radical, $R_5$ denotes hydrogen, alkyl, nitro or halogen,
ii) anthraquinone dyes of following formula B:

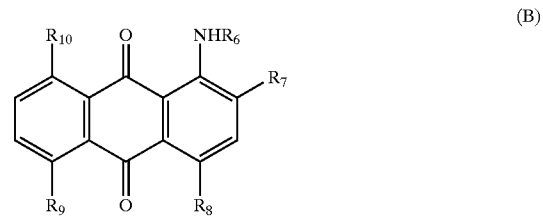

(B)

in which $R_6$ denotes hydrogen or a monohydroxyalkyl or polyhydroxyalkyl radical, $R_7$ denotes hydrogen or an alkyl or alkoxy radical, $R_8$ denotes hydrogen or a hydroxyl, amino, monohydroxyalkylamino or polyhydroxyalkylamino radical, $R_9$ and $R_{10}$, which are identical or different, are hydrogen, hydroxyl or amino, iii) azo dyes of following formula (C):

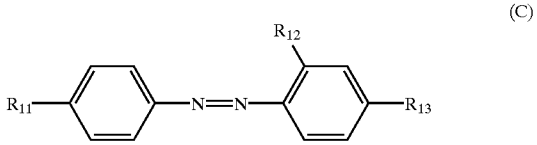

in which:
- $R_{11}$ denotes a nitro or amino radical or an amino radical mono- or disubstituted by alkyls,
- $R_{12}$ denotes hydrogen or an alkyl radical,
- $R_{13}$ denotes an amino radical or an amino radical mono- or disubstituted by monohydroxyalkyls, it being understood that the alkyl and alkoxy radicals mentioned hereinabove in the formulae (A), (B) and (C) are $C_1$–$C_4$ radicals and that they can be linear or branched, and the cosmetically acceptable salts of all these compounds.

The term "$C_1$–$C_4$" is understood to mean in particular the methyl, ethyl, n-propyl, isopropyl, n-butyl, sec-butyl and tert-butyl radicals.

The term "cosmetically acceptable salts" denotes more particularly the hydrochlorides, hydrobromides and sulphates.

More advantageously still, according to the present invention, it is preferable to employ the following direct dyes:
- 1-amino-2-nitro-4-N—(β-hydroxyethyl)amino-5-methylbenzene,
- 1,4,5,8-tetraaminoanthraquinone,
- 1,4-bis-N,N'-[(β, γ-dihydroxypropyl)amino]-anthraquinone,
- 1,4,4-N-tris(β-hydroxyethyl)-1,4-diamino-2-nitrobenzene,
- 1-N-(β-hydroxyethyl)amino-2-nitro-4-aminobenzene,
- 1-hydroxy-3-nitro-4-aminobenzene,
- 1-hydroxy-3-nitro-4-N-(β-hydroxyethyl)aminobenzene,
- 1-(β-hydroxyethyloxy)-3-methylamino-4-nitrobenzene,
- 1-methylamino-2-nitro-5-(β, γ-dihydroxypropyloxy)benzene,
- 1-N-(β-aminoethyl)amino-2-nitro-4-(β-hydroxyethyloxy)benzene,
- 4-[N-ethyl-N-(β-hydroxyethyl)amino]-1-N-(β-hydroxyethyl)amino-2-nitrobenzene,
- 1-(4'-aminodiphenylazo)-2-methyl-4-N-bis(β-hydroxyethyl)aminobenzene,
- 1-methoxy-3-N-(β-aminoethyl)amino-4-nitrobenzene,
- 1-amino-2-nitro-4-N-(β-hydroxyethyl)aminobenzene,
- 1-amino-2-nitro-4-N-bis(β-hydroxyethyl)aminobenzene,
- 1,4-N-bis(β-hydroxyethyl)amino-5-nitrobenzene,
- 1,4-diaminoanthraquinone,
and their cosmetically acceptable salts.

Other preferred cationic dyes are those of Arianor type (Basic Brown 17, Basic Brown 16, Basic Yellow 57, Basic Blue 99) and the cationic dyes disclosed in the Ciba Patents WO 95/01772, WO 95/15144 and EP 714,954.

The direct dyes, in the base or salified form, are generally present in the dyeing composition according to the invention in proportions which can range from approximately 0.001 to approximately 10% and preferably from approximately 0.05 to approximately 5% by weight with respect to the total weight of the composition.

The present invention also relates to a composition for the oxidation dyeing of keratinous fibres and in particular of human keratinous fibres, such as the hair, comprising, in a medium appropriate for dyeing, at least one polymer as defined hereinabove and at least one oxidation dye precursor and/or melanin precursors.

The oxidation dye precursors can be chosen in particular from para-phenylenediamines, para-aminophenols, ortho-phenylenediamines and heterocyclic bases, such as, for example, pyridine derivatives, pyrimidine derivatives, pyrazole derivatives, pyrazolopyrimidine derivatives, indoles or indolines, and their acid addition salts.

These compositions can also include couplers, which can be chosen in particular from meta-phenylenediamines, meta-aminophenols, meta-diphenols, heterocyclic couplers, such as, for example, indole derivatives, indoline derivatives, benzimidazole derivatives, benzomorpholine derivatives, sesamol derivatives or pyridine, pyrimidine and pyrazole derivatives, and their addition salts with an acid.

Generally, the addition salts with an acid which can be used in the context of dyeing compositions are chosen in particular from the hydrochlorides, hydrobromides, sulphates, citrates, succinates, tartrates, lactates and acetates.

The medium appropriate for direct or oxidation dyeing (or support) is generally composed of water or of a mixture of water and of at least one organic solvent, in order to dissolve the compounds which would be insufficiently soluble in water.

Mention may be made, as organic solvent, of, for example, lower alkanols, such as ethanol and isopropanol; glycerol; glycols and glycol ethers, such as 2-butoxyethanol, propylene glycol, propylene glycol monomethyl ether, diethylene glycol monoethyl ether and diethylene glycol monomethyl ether; and aromatic alcohols, such as benzyl alcohol or phenoxyethanol, the analogous products and their mixtures.

When they are present, the oxidation base or bases preferably represent from 0.0005 to 12% by weight approximately of the total weight of the dyeing composition.

When they are present, the coupler or couplers preferably represent from 0.0001 to 10% by weight approximately of the total weight of the dyeing composition.

The polymers of the invention preferably represent from 0.01 to 10% by weight approximately of the total weight of the direct or oxidation dyeing composition and preferably from 0.1 to 5%.

The solvents can be present in proportions preferably of between 1 and 40% by weight approximately with respect to the total weight of the dyeing composition and more preferably still between 5 and 30% by weight approximately.

The pH of the dyeing compositions is generally between 3 and 12 approximately and preferably between 5 and 11. It can be adjusted to the desired value by means of acidifying or basifying agents commonly used in the dyeing of keratinous fibres.

Mention may be made, among the acidifying agents, by way of example, of inorganic or organic acids, such as hydrochloric acid, orthophosphoric acid, sulphuric acid, carboxylic acids, such as acetic acid, tartaric acid, citric acid or lactic acid, or sulphonic acids.

Mention may be made, among the basifying agents, by way of example, of aqueous ammonia, alkaline carbonates, alkanolamines, such as mono-, di- and triethanolamines and their derivatives, sodium hydroxide, potassium hydroxide and the compounds of following formula:

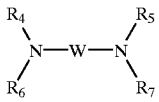

in which W is a propylene residue optionally substituted by a hydroxyl group or a $C_1$–$C_6$ alkyl radical and $R_4$, $R_5$, $R_6$ and $R_7$ which are identical or different, represent a hydrogen atom or a $C_1$–$C_6$ alkyl or $C_1$–$C_6$ hydroxyalkyl radical.

The dyeing compositions comprising a protective agent can also include various adjuvants conventionally used in hair dyeing compositions.

The oxidizing compositions used in oxidation dyeing which constitute another subject-matter of the invention can also comprise an unsaturated heterocyclic quaternary polymer as defined hereinabove and at least one oxidizing agent.

These oxidizing agents can be chosen in particular from hydrogen peroxide, urea hydrogen peroxide, alkali metal bromates, persalts, such as perborates and persulphates, and enzymes, such as peroxidases and two-electron oxidoreductases.

Another subject-matter of the invention is a hair dyeing process, characterized in that a composition as defined hereinabove comprising the protective agent in accordance with the invention, optionally with an oxidizing composition in the case of oxidation dyeing, is applied to the hair in an amount sufficient to dye the hair. In the case of oxidation dyeing, only the composition comprising the dye precursors or the oxidizing composition can include a polymer according to the invention. The composition is allowed to act for a time of between 5 and 45 minutes approximately and then the hair is rinsed.

For direct dyeing, a composition as defined hereinabove comprising at least one direct dye is applied to the hair in an amount sufficient to produce a colouring and is allowed to act for a time of between 10 and 60 min approximately. The hair is then rinsed.

It is also possible to carry out direct dyeings without rinsing.

Another subject-matter of the present invention is a bleaching composition comprising, in a medium appropriate for bleaching, an agent for bleaching the hair and a protective agent as defined hereinabove.

Use is made, in bleaching the hair, of bleaching agents known per se, such as hydrogen peroxide, persulphates, sodium percarbonate, or perborates.

To bleach the hair, a bleaching composition as defined hereinabove is applied to the hair in an amount and for a time sufficient to bleach the hair. The hair is subsequently rinsed.

The invention also relates to compositions intended for the cosmetic treatment of the hair comprising a novel heterocyclic quaternary polymer as defined in the formulae VII, VIII and IX.

The examples which follow are intended to illustrate the invention.

Tables 1 and 2 hereinbelow are intended to illustrate the preparation of polymers used according to the invention.

The information relating to the structure of the compound of the polymer of formula (I) is successively shown in these tables.

TABLE 1

|  | $A^P_1$ | $A^P_2$ | $B_1$ | $B_2$ | $A^\sigma$ |
|---|---|---|---|---|---|
| Ex. 1 | imidazole of formula (IV) with $R_3 = R_4 = R_5 = H$ | imidazole of formula (IV) with $R_3 = R_4 = R_5 = H$ | —(CH$_2$)$_3$— | —(CH$_2$)$_3$— | Br$^-$ |
| Ex. 2 | imidazole of formula (IV) with $R_3 = R_4 = R_5 = H$ | imidazole of formula (IV) with $R_3 = R_4 = R_5 = H$ | —(CH$_2$)$_4$— | —(CH$_2$)$_3$— | Br$^-$ |
| Ex. 3 | imidazole of formula (IV) with $R_3 = H$; $R_4$ and $R_5$ form an aromatic $C_6$ ring | imidazole of formula (IV) with $R_3 = H$; $R_4$ and $R_5$ form an aromatic $C_6$ ring | —(CH$_2$)$_4$— | —(CH$_2$)$_3$— | Br$^-$ |
| Ex. 4 | imidazole of formula (IV) with $R_3 = R_4 = R_5 = H$ | of-imidazole of formula (IV) with $R_3 = R_4 = R_5 = H$ | —(CH$_2$)$_4$— | 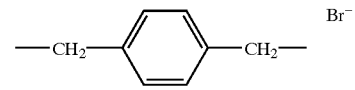 | Br$^-$ |
| Ex. 5 | imidazole of formula (IV) with $R_3 = R_4 = R_5 = H$ | imidazole of formula (IV) with $R_3 = R_4 = R_5 = H$ | —(CH$_2$)$_4$— | —(CH$_2$)$_2$—O—(CH$_2$)$_2$—O—(CH$_2$)$_2$— | Cl$^-$ |
| Ex. 6 | imidazole of formula (IV) with $R_3 = R_4 = R_5 = H$ | imidazole of formula (IV) with $R_3 = R_4 = R_5 = H$ | —(CH$_2$)$_2$—O—(CH$_2$)$_2$—O—(CH$_2$)$_2$— | —(CH$_2$)$_2$—O—(CH$_2$)$_2$—O—(CH$_2$)$_2$— | Cl$^-$ |
| Ex. 7 | imidazole of formula (IV) with $R_3 = R_4 = R_5 = H$ | of-imidazole of formula (IV) with $R_3 = R_4 = R_5 = H$ | —(CH$_2$)$_2$—O—(CH$_2$)$_2$—O—(CH$_2$)$_2$— | 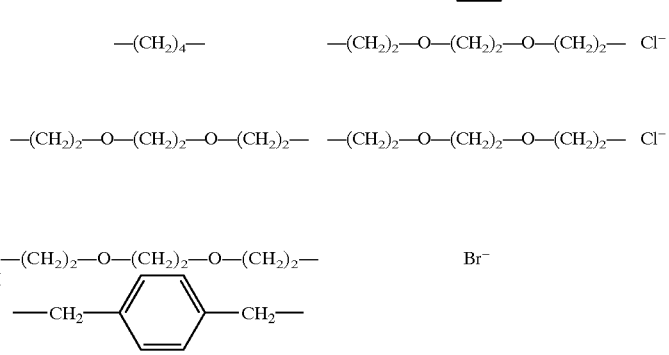 | Br$^-$ |

TABLE 1-continued

| | A$^p_1$ | A$^p_2$ | B$_1$ | B$_2$ | A$^\sigma$ |
|---|---|---|---|---|---|
| Ex.8 | imidazole of formula (IV) with R$_3$ = R$_4$ = R$_5$ = H | offor-imidazole of formula (IV) with R$_3$ = R$_4$ = R$_5$ = H | —CH$_2$—C$_6$H$_4$—CH$_2$— | —CH$_2$—C$_6$H$_4$—CH$_2$— | Br$^-$ |
| Ex.9 | imidazole of formula (IV) with R$_3$ = R$_4$ = R$_5$ = H | offor-imidazole of formula (IV) with R$_3$ = R$_4$ = R$_5$ = H | —(CH$_2$)$_4$— | —CH$_2$—C$_6$H$_4$—CH$_2$— | Cl$^-$ |

TABLE 2

| | A$^p_1$ | A$^p_2$ | B$_1$ | B$_2$ | X$^\sigma$ |
|---|---|---|---|---|---|
| Ex. 10 | quaternary ammonium of formula (III) with R1 = R2 = CH$_3$ | imidazole of formula (IV) with R$_3$ = R$_4$ = R$_5$ = H | —(CH$_2$)$_3$— | —(CH$_2$)$_6$— | Cl$^-$ |
| Ex.11 | quaternaryammonium offormula (III) with R$_1$ = R$_2$ = CH$_3$ | imidazole of formula (IV) with R$_3$ = R$_4$ = R$_5$ = H | —(CH$_2$)$_3$— | —CH$_2$—C$_6$H$_4$—CH$_2$— | Cl$^-$ |
| Ex.12 | quaternaryammonium offormula (III) with R$_1$ + R$_2$ = (CH$_2$)$_5$ | imidazole of formula (IV) with R$_3$ = R$_4$ = R$_5$ = H | —(CH$_2$)$_3$— | —CH$_2$—C$_6$H$_4$—CH$_2$— | Cl$^-$ |
| Ex. 13 | imidazole of formula (IV) with R$_3$ = phenyl and R$_4$ + R$_5$ = H | imidazole of formula (IV) with R$_3$ = phenyl and R$_4$ + R$_5$ = H | —(CH$_2$)$_4$— | —(CH$_2$)$_4$— | Br$^-$ |
| Ex.14 | pyrazole offormula (V) with R6 = R$_7$ = R$_8$ = H | offormulapyrazole of formula(V) with R6 = R$_7$ = R$_8$ = H | —(CH$_2$)$_4$— | —CH$_2$—C$_6$H$_4$—CH$_2$— | Cl$^-$ |

1) Synthesis of Example 1 a) Synthesis of the Diamine 1,1'-(1,3-Propanediyl) bisimidazole 35.4 g (0.52 mol) of imidazole, a solution of 100 g (2.5 mol) of sodium hydroxide in 100 ml of water, 5.15 g of tetrabutylammonium bromide and 52.49 g (0.26 mol) of 1,3-dibromopropane in solution in 240 ml of toluene are introduced into a reactor equipped with a mechanical stirrer, a thermometer and a reflux condenser. This mixture is brought to reflux for 32 hours. After cooling, 150 ml of water are added to the mixture. The reaction mixture then exhibits three liquid phases. After separating by settling, the intermediate phase, which is insoluble in the usual organic solvents, is recovered and is distilled. 27.5 g of slightly yellow transparent oil are thus separated.

The results obtained by DMSO proton NMR are as follows:

δ 2.22 (m, 2H), δ 3.92 (t, 4H), δ 6.91 (m, 2H), δ 7.17 (m, 2H), δ 7.61 (m, 2H)

b) Synthesis of the Polymer

A mixture of 17.6 g (0.1 mol) of the diamine obtained hereinabove, 100 ml of methanol and 20.2 g (0.1 mol) of 1,3-dibromopropane is brought to reflux for 10 hours. After evaporating the solvent, the residue is ground in 300 ml of isopropyl ether until a powder is obtained, which powder is filtered off and dried under vacuum in the presence of phosphorus pentoxide. 34.6 g of a hydroscopic beige powder are thus obtained with a yield of 91.5%. Quantitative determination of the bromides by AgNO$_3$: 40.4% (theory: 42.3%)

2) Synthesis of Example 2 a) Synthesis of the Diamine 1,1'-(1,4-Butanediyl) bisimidazole 35.4 g (0.52 mol) of imidazole, a solution of 100 g (2.5 mol) of sodium hydroxide in 100 ml of water, 5.15 g of tetrabutylammonium bromide and 54 g (0.26 mol) of 1,4-dibromobutane in solution in 240 ml of toluene are introduced into a reactor equipped with a mechanical stirrer, a thermometer and a reflux condenser. This mixture is brought to reflux for 6 hours. After cooling, the expected diamine crystallizes and is filtered off and the cake obtained is washed with 100 ml of toluene and then with 2 times 50 ml of ice-cold water. The product, thus washed, is recrystallized from 200 ml of water. After drying, 44 g of light beige powder are obtained (yield: 89%). An analysis by DMSO proton NMR gave the following results:

δ 1.61–1.68 (m, 4H), δ 3.96–4.02 (m, 4H), δ 6.91 (m, 2H), δ 7.17 (m, 2H), δ 7.64 (m, 2H)

b) Synthesis of the Polymer

A mixture composed of 24.73 g (0.13 mol) of the diamine obtained hereinabove, 210 ml of methanol and 26.25 g (0.13 mol) of 1,3-dibromopropane is brought to reflux for 56 hours. After evaporating the solvent, the residue is ground in 300 ml of isopropyl ether until a powder is obtained, which powder is filtered off and dried under vacuum in the presence of phosphorus pentoxide. The beige powder obtained (39.9 g; yield: 100%) is hygroscopic. Quantitative determination of the bromides by $AgNO_3$: 38% (theory: 40.7%).

3) Synthesis of Example 3 a) Synthesis of the Diamine 1,1'-(1,4-butanediyl) bisbenzimidazole 12.95 g (0.06 mol) of 1,4-dibromobutane are added dropwise at room temperature to a mixture of 31.4 g (0.78 mol) of ground potassium hydroxide, 14 g (0.12 mol) of benzimidazole and 200 ml of acetone and stirring is maintained at this temperature for 8 hours; the precipitate formed is then filtered off and is recrystallized directly from 50 ml of ethanol. 9.7 g of white powder are thus obtained with a melting point at 175° C.

$CDCl_3$ proton NMR analysis gave the following results: δ 1.87–1.92 (m, 4H), δ 4.1–4.16 (m, 4H), δ 7.24–7.3 (m, 6H), δ 7.77–7.84 (m, 4H).

b) Synthesis of the Polymer

A mixture of 7.31 g (0.025 mol) of 1,1'-(1,4-butanediyl) bisbenzimidazole, 50 ml of methanol and 5.05 g (0.025 mol) of 1,3-dibromopropane is brought to reflux for 40 hours. The reaction mixture is concentrated and then the residue is taken up in isopropyl ether; after filtering and drying, 12.3 g of white powder are obtained; % Br 31.65 (theory 32.3%).

4) Synthesis of Example 4 in Aqueous Solution

A mixture of 20.37 g (0.1 mol) of 1,1'-(1,4-butanediyl) bisimidazole comprising 6.6% of water, 25 ml of water and 26.4 g (0.1 mol) of α, α'-dibromo-para-xylene is brought to 110° C. for 5 hours in a hermetically sealed reactor. Quantitative determination by silver nitrate of a test sample shows that 98.3% of the bromides are in the ionic form after reacting for 5 h. The solution is adjusted to 50% of active material by taking into account the level of bromides. Quantitative determination of the bromides by $AgNO_3$: 33.9% (theory: 35.2%) on a dry basis.

5) Synthesis of Example 5 in Aqueous Solution

A mixture of 40.73 g (0.2 mol) of 1,1'-(1,4-butanediyl) bisimidazole comprising 6.6% of water, 100 ml of water and 38.6 g (0.2 mol) of 97% 1,2-bis(2-chloroethoxy)ethane (Aldrich) is brought to reflux for 8 hours. Quantitative determination by silver nitrate of a test sample shows that 97.8% of the chlorides are in the ionic form after reacting for 8 hours. The reaction mixture is concentrated slightly under vacuum in the presence of vegetable charcoal, the charcoal is filtered off and then the solution is adjusted to 50% of active material by taking into account the level of chlorides. 127 g of slightly amber solution are obtained.

Quantitative determination of the chlorides by $AgNO_3$: 18.5% (theory: 18.8%) on a dry basis.

6) Synthesis of Example 6 in Aqueous Solution

A mixture of 5.26 g at 95% (0.02 mol) of 1,1'-(1,2-bis(ethoxy)ethanediyl)bisimidazole, 10 ml of water and 3.74 g (0.02 mol) of 97% 1,2-bis(2-chloroethoxy)ethane (Aldrich) is brought to reflux for 21 hours. Quantitative determination by silver nitrate of a test sample shows that 96% of the chlorides are in the ionic form after reacting for 21 hours. The solution is then adjusted to 50% of active material by taking into account the level of chlorides. 15.5 g of light yellow solution are obtained.

Quantitative determination of the chlorides by $AgNO_3$ in the light yellow solution: 2.28 meq/g.

7) Synthesis of Example 7 in Aqueous Solution

A mixture of 3.95 g (0.015 mol) of 1,1'-(1,2-bis(ethoxy) ethanediyl)bisimidazole, 10 ml of water and 3.96 g (0.015 mol) of α,α'-dibromo-para-xylene is brought to reflux for 5 hours. Quantitative determination by silver nitrate of a test sample shows that 100% of the bromides are in the ionic form after reacting for 5 hours. The solution is filtered, is concentrated slightly under vacuum and is then adjusted to 50% of active material by taking into account the level of bromides. 14.8 g of amber-yellow solution are obtained.

Quantitative determination of the bromides by $AgNO_3$: 1.94 meq/g of solution.

8) Synthesis of Example 8

A mixture of 2.38 g (0.01 mol) of 1,1'-(α, α'-para-xylene) bisimidazole, 9 ml of water and 2.6 g (0.01 mol) of α, α'-dibromo-para-xylene is brought to reflux for 10 hours. Quantitative determination by silver nitrate of a test sample shows that 100% of the bromides are in the ionic form after reacting for 10 hours. The reaction mixture is concentrated and then the residue is taken up in 10 ml of methanol; the beige powder is filtered off. After drying under vacuum, 3.6 g of beige powder are obtained.

9) Synthesis of Example 9 in Aqueous Solution

A mixture of 20.37 g (0.1 mol) of 1,1'-(1,4-butanediyl) bisimidazole comprising 6.6% of water, 50 ml of water and 17.5 g (0.1 mol) of α, α'-dichloro-para-xylene is brought to reflux for 5 hours. Quantitative determination by silver nitrate of a test sample shows that 97% of the chlorides are in the ionic form after reacting for 3 hours. The reaction mixture is left at 95° C. for a further 2 hours. The solution is then adjusted to 50% of active material by taking into account the level of chlorides. 68.4 g of solution are obtained.

Quantitative determination of the chlorides by $AgNO_3$: 18.8% (theory 19.4%) on a dry basis.

10) Synthesis of Example 10

A mixture of 15.94 g (0.1 mol) of 96% N,N-dimethyl-1H-imidazole-1-propanamine, 40 ml of methanol and 15.5 g (0.1 mol) of 1,6-dichlorohexane is brought to reflux for 122 hours. Quantitative determination by silver nitrate of a test sample shows that 96% of the chlorides are in the ionic form after reacting for 122 hours. The solution is concentrated and the residue is dried under a vacuum of 0.1 mmHg. 30 g of very hygroscopic white powder are obtained.

Quantitative determination of the chlorides by $AgNO_3$: 22.0% (theory: 22.9%).

11) Synthesis of Example 11

A mixture of 2.51 g (0.0164 mol) of N,N-dimethyl-1H-imidazole-1-propanamine, 8.2 ml of methanol and 2.87 g (0.0164 mol) of α, α'-dichloro-para-xylene is brought to reflux for 5 hours. Quantitative determination by silver nitrate of a test sample shows that 94% of the chlorides are in the ionic form after reacting for 5 hours. The reaction mixture is left at 95° C. for a further 2 hours. The solution is concentrated and the residue is dried under vacuum. 5.4 g of very hygroscopic white powder are obtained.

Quantitative determination of the chlorides by $AgNO_3$: 19.5% (theory: 21.6%).

12) Synthesis of Example 12

A mixture of 6.95 g (0.036 mol) of 1-(1H-piperidyl)-3-(1H-imidazolyl)propane, 15 ml of methanol and 6.3 g (0.036 mol) of α, α'-dichloro-para-xylene is brought to reflux for 6 hours. Quantitative determination by silver nitrate of a test sample shows that 100% of the chlorides are in the ionic form after reacting for 6 hours. The solution is concentrated and the residue is dried under vacuum. 13 g of hygroscopic slightly pinkish powder are obtained.

Quantitative determination of the chlorides by $AgNO_3$: 18.3% (theory: 19.2%).

13) Synthesis of Example 13

A mixture composed of 5.32 g (0.015 mol) of 96.6% 1,1'-(1,4-butanediyl)bis(2-phenylimidazole), 10 ml of water and 3.24 g (0.015 mol) of 1,4-dibromobutane is brought to reflux for 6 hours. Quantitative determination by silver nitrate of a test sample shows that 100% of the bromides are in the ionic form after reacting for 6 hours. The solution is filtered, is slightly concentrated under vacuum and is then adjusted to 50% of active material by taking into account the level of bromides. 8 g of light yellow solution are obtained.

Quantitative determination of the bromides by $AgNO_3$: 1.79 meq/g of solution.

14) Synthesis of Example 14

A mixture of 19.02 g (0.1 mol) of 1,1'-(1,4-butanediyl) bispyrazole, 40 ml of water and 17.5 g (0.1 mol) of α, α'-dichloro-para-xylene is brought to reflux for 3.5 hours. Quantitative determination by silver nitrate of a test sample shows that 99% of the chlorides are in the ionic form after reacting for 3.5 hours. Approximately 40 ml of water are added, the cloudy light material is filtered off and the solution is concentrated and adjusted to 50% of active material by taking into account the level of chlorides. 73 g of solution are obtained.

Quantitative determination of the chlorides by $AgNO_3$: 17.96% (theory: 19.4%) on a dry basis.

The following examples are intended to illustrate the compositions and the application of the polymers in accordance with the invention.

APPLICATIONAL EXAMPLE 1

The following composition is prepared:

| | | |
|---|---|---|
| Aqueous solution of polymer of Example 9 comprising 50% of AM | | 3 g |
| Thioglycolic acid | | 5 g |
| Monoethanolamine | | 2.6 g |
| Fragrance | | 0.5 g |
| Oxyethylenated oleyl alcohol (20 mol of ethylene oxide) | | 1 g |
| Cocoyl amidopropyl dimethyl hydroxypropyl sulphobetaine, as a 50% aqueous solution | | 2 g |
| Diethylenetriaminepentaacetic acid, pentasodium salt, as a 40% aqueous solution | | 0.2 g |
| Demineralized water | q.s. | 100 g |

This composition is used as a reducing composition.

This composition is applied to wet hair wound beforehand on hair-setting rollers. After having allowed the composition to act for approximately 15 minutes, the hair is rinsed copiously with water and then the following oxidizing composition is applied:

Aqueous hydrogen peroxide solution q.s. for 8 volumes

The oxidizing composition is allowed to act for approximately 5 minutes, the hair is then rinsed copiously with water and the rollers are removed.

After drying under a hairdryer, the hair exhibits beautiful curls.

APPLICATIONAL EXAMPLE 2

The following oxidizing composition is prepared:

| | | |
|---|---|---|
| Aqueous solution of polymer of Example 4 comprising 50% of AM | | 1 g |
| 50% Aqueous hydrogen peroxide solution | | 4.8 g |
| Stabilizers | | 0.2 g |
| Citric acid | q.s. | pH 3 |
| Demineralized water | q.s. | 100 g |

The following reducing composition is applied:

| | |
|---|---|
| Thioglycolic acid | 5 g |
| Monoethanolamine | 2.6 g |
| Fragrance | 0.5 g |
| Oxyethylenated oleyl alcohol (20 mol of ethylene oxide) | 1 g |
| Cocoyl amidopropyl dimethyl hydroxypropyl sulphobetaine, as a 50% aqueous solution | 2 g |
| Diethylenetriaminepentaacetic acid, pentasodium salt, as a 40% aqueous solution | 0.2 g |
| Demineralized water q.s. | 100 g |

This composition is applied to wet hair wound beforehand on hair-setting rollers. After having allowed the composition to act for approximately 15 minutes, the hair is rinsed copiously with water and then the oxidizing composition prepared hereinabove is applied.

The oxidizing composition is allowed to act for approximately 5 minutes, the hair is then rinsed copiously with water and the rollers are removed.

After drying under a hairdryer, the hair exhibits beautiful curls.

APPLICATIONAL EXAMPLE 3

The following composition is prepared:

| | |
|---|---|
| Octyldodecanol, sold under the name Eutanol D by the company Henkel | 8 g |
| Oleic acid | 20 g |
| Monoethanolamine lauryl ether sulphate, sold under the name Sipon LM 35 by the company Henkel | 3 g |
| Ethyl alcohol | 10 g |
| Benzyl alcohol | 10 g |
| Cetearyl alcohol comprising 33 mol of ethylene oxide, sold under the name Simulsol GS by the company Seppic | 2.4 g |
| Ethylenediaminetetraacetic acid | 0.2 g |
| Aqueous solution of polymer of Example 4 comprising 50% of A.M. | 3.7 g |
| Monoethanolamine | 7.5 g |

-continued

| | |
|---|---|
| Linoleic acid diethanolamide, sold under the name Comperlan F by the company Henkel | 8 g |
| Aqueous ammonia comprising 20% of NH$_3$ | 10.2 g |
| Sodium metabisulphite, as a 35% aqueous solution | 1.3 g |
| Hydroquinone | 0.15 g |
| 1-Phenyl-3-methyl-5-pyrazolone | 0.2 g |
| para-Phenylenediamine | 0.8 g |
| meta-Aminophenol | 0.05 g |
| 2-Methyl-5-N-(β-hydroxyethyl)aminophenol | 2.8 g |
| 2,4-Diaminophenoxyethanol dihydrochloride | 0.15 g |
| Demineralized water     q.s. for | 100 g |

This composition is used for the oxidation dyeing of the hair.

The composition obtained is mixed, weight for weight, with aqueous hydrogen peroxide solution assaying 20 volumes and with a pH of 3.

The mixture thus prepared is applied to permed or unpermed grey hair comprising 90% of white hairs for 30 min at the rate of 28 g per 3 g of hair.

The hair is subsequently rinsed, washed with a standard shampoo and dried.

The hair has a red ash-chestnut (deep purple chestnut) colouring.

It is soft to the touch, shiny and disentangles easily.

APPLICATIONAL EXAMPLE 4

The following composition is prepared:

| | |
|---|---|
| Cetearyl alcohol (C$_{16}$/C$_{18}$, 50/50), sold under the name Lanette Wax 0 by the company Henkel | 18 g |
| 2-Octyldodecanol | 3 g |
| Oxyethylenated (15 EO) cetearyl alcohol (C$_{16}$/C$_{18}$, 35/65), sold under the name Mergital CS 15 by the company Sinnova-Henkel | 3 g |
| Ammonium lauryl sulphate comprising 30% of A.M. | 12 g |
| Aqueous solution of polymer of Example 4 comprising 50% of A.M. | 3 g |
| Ammonium thiolactate comprising 50% of thiolactic acid equivaient | 0.8 g |
| Aqueous ammonia comprising 20% of NH$_3$ | 12 g |
| para-Toluylenediamine | 1.5 g |
| Resorcinol | 0.6 g |
| meta-Aminophenol | 0.25 g |
| para-Aminophenol | 0.20 g |
| 2,4-Diaminophenoxyethanol dihydrochloride | 0.15 g |
| Demineralized water     q.s. for | 100 g |

This composition is provided in the form of a cream.

The composition obtained is diluted at the time of use with 1.5 times its volume of 30 volume aqueous hydrogen peroxide solution with a pH of 3.

The mixture thus prepared is applied to permed or unpermed grey hair comprising 90% of white hairs for 30 min at the rate of 28 g per 3 g of hair. The hair is subsequently rinsed, washed with a standard shampoo and dried.

The hair has a dark chestnut colouring.

It is soft to the touch, shiny and disentangles easily.

APPLICATIONAL EXAMPLE 5

The following composition is prepared:

| | |
|---|---|
| Octyldodecanol, sold under the name Eutanol D by the company Henkel | 8 g |
| Oleic acid | 20 g |
| Monoethanolamine lauryl ether sulphate, sold under the name Sipon LM 35 by the company Henkel | 3 g |
| Ethyl alcohol | 10 g |
| Benzyl alcohol | 10 g |
| Cetearyl alcohol comprising 33 mol of ethylene oxide, sold under the name Simulsol GS by the company Seppic | 2.4 g |
| Ethylenediaminetetraacetic acid | 0.2 g |
| Aqueous solution of polymer of Example 4 comprising 50% of A.M. | 3.7 g |
| Monoethanolamine | 9.5 g |
| Linoleic acid diethanolamide, sold under the name Comperlan F by the company Henkel | 8 g |
| Sodium metabisulphite, as a 35% aqueous solution | 1.3 g |
| Hydroquinone | 0.15 g |
| 1-Phenyl-3-methyl-5-pyrazolone | 0.2 g |
| para-Toluylenediamine | 0.9 g |
| Resorcinol | 0.2 g |
| 2,4-Diaminophenoxyethanol dihydrochloride | 2.5 g |
| Demineralized water     q.s. for | 100 g |

The composition obtained is mixed, weight for weight, with aqueous hydrogen peroxide solution assaying 20 volumes with a pH of 3.

The mixture thus prepared is applied to permed or unpermed grey hair comprising 90% of white hairs for 30 min at the rate of 28 g per 3 g of hair.

The hair is subsequently rinsed, washed with a standard shampoo and dried.

The hair has an intense bluish-black colouring.

It is soft to the touch, shiny and disentangles easily.

What is claimed is:

1. A polymer comprising at least one unit of formula (VII):

wherein:

A$_1^+$, which may be identical or different, is chosen from unsaturated quaternary heterocycles of formula (II):

wherein:

E, G, L, and J, which may be identical or different, are each chosen from
a carbon atom, an oxygen atom, a sulphur atom, and a nitrogen atom,
wherein at least one of E, G, L, and J is a nitrogen atom;
and further wherein when at least one of E, G, L, and J is a carbon atom, said carbon atom may optionally be substituted by at least one substituent chosen from halogen atoms, hydroxyl groups, nitro groups, cyano groups, mercapto groups, carboxyl groups, alkyl groups, monohydroxyalkyl groups, polyhydroxyalkyl groups, thioalkyl groups, cyanoalkyl groups, alkoxy groups, acyl groups, acetyloxy groups, cycloalkyl groups, optionally substituted, aryl groups, optionally substituted, alkylaryl groups, optionally substituted, and groups having the formula —NHR$_N$ wherein R$_N$ is chosen from a hydrogen atom, alkyl groups, monohydroxyalkyl groups, polyhydroxyalkyl groups, acetyl groups, and ureido groups;

with the proviso that when at least two of said E, G, L, and J are nitrogen atoms, then at least one of said at least two of said E, G, L, and J may be substituted with a substituent chosen from a hydrogen atom, alkyl groups, monohydroxyalkyl groups, polyhydroxyalkyl groups, aryl groups, optionally substituted, and alkylaryl groups, optionally substituted; and with the further proviso that when at least two of E, G, L, and J are substituted, the substituents may optionally also form, together with the atoms to which they are attached, at least one 5- to 7-membered aromatic ring, optionally substituted;

$A_2^+$, which may be identical or different, is chosen from quaternary ammoniums of formula (III):

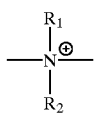  (III)

wherein:
R$_1$ and R$_2$, which may be identical or different, are each chosen from carboxyl groups, alkyl groups, polyhydroxyalkyl groups, thioalkyl groups, cyanoalkyl groups, alkoxy groups, acyl groups, acetyloxy groups, cycloalkyl groups, optionally substituted, aryl groups, optionally substituted, alkylaryl groups, optionally substituted, and groups having the formula —NHR$_N$ wherein R$_N$ is chosen from a hydrogen atom, alkyl groups, monohydroxyalkyl groups, polyhydroxyalkyl groups, acetyl groups, and ureido groups;

wherein R$_1$ and R$_2$ may optionally also form, together with the nitrogen atom to which they are attached, at least one saturated 5- to 7-membered carbon-based ring;

B$_1$ and B$_2$, which may be identical or different, are each chosen from hydrocarbons optionally having at least one substituent chosen from optionally substituted aromatic rings, an oxygen atom, a sulphur atom, a nitrogen atom, an —SO— group, an —SO$_2$— group, an —SO$_3$H group, amino groups, alkylamino groups, hydroxyl groups, quaternary ammonium groups, and ureido groups, wherein said at least one substituent is bonded to or inserted in the main chain of said polymer, with the proviso that at least one of said B$_1$ and B$_2$ is chosen from groups other than —CH$_2$—CHOH—CH$_2$—; and X$^-$ is chosen from halide anions and anions derived from at least one acid chosen from organic acids and inorganic acids.

2. A polymer according to claim 1, wherein at least one of said B$_1$ and B$_2$, which may be identical or different, is chosen from groups of formula (VI):

—(CH$_2$)$_n$—CO—A—OC—(CH$_2$)$_n$—   (VI)

wherein:
n is an integer ranging from 1 to 10;
A is chosen from:
(a) glycol residues of formula: —O—Z—O— in which Z is chosen from hydrocarbons, and groups having the formula:

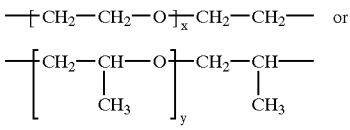

wherein x and y, which may be identical or different, are each a number ranging from 1 to 4;
(b) bis(secondary amine) groups;
(c) bis(primary amine) groups having the formula:

—NH—Y—NH— wherein Y is chosen from hydrocarbons, and groups having the formula —(CH$_2$)$_2$—S—S—(CH$_2$)$_2$—; and
(d) ureylene groups.

3. A polymer according to claim 2, wherein n is an integer from 1 to 6.

4. A polymer according to claim 1, wherein said B$_1$ and B$_2$, which may be identical or different, are each chosen from:
(a) groups having the formula:

—(CH$_2$)$_n$— wherein n is an integer ranging from 1 to 6;
(b) groups having the formula:

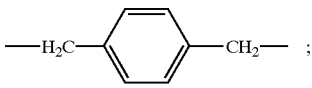

and
(c) groups having the formula:

—(CH$_2$)$_2$—O—(CH$_2$)$_2$—O—(CH$_2$)$_2$—.

5. A polymer according to claim 1, wherein said polymer has a mass-average molecular weight ranging from 1000 to 20,000.

6. A polymer according to claim 1, wherein said halogen atoms are chosen from fluorine, chlorine, bromine, and iodine.

7. A polymer according to claim 1, wherein said alkyl groups, said monohydroxyalkyl groups, said polyhydroxyalkyl groups, and said hydrocarbons are each linear, branched or cyclic.

8. A polymer according to claim 1, wherein said alkyl groups comprise from 1 to 20 carbon atoms.

9. A polymer according to claim 8, wherein said alkyl groups are chosen from methyl groups, ethyl groups, propyl groups, isopropyl groups, n-propyl groups, butyl groups, n-butyl groups, tert-butyl groups, pentyl groups, n-pentyl groups, isopentyl groups, n-hexyl groups, isohexyl groups, heptyl groups, octyl groups, nonyl groups, decyl groups, undecyl groups, dodecyl groups, and pentadecyl groups.

10. A polymer according to claim 8, wherein said alkyl groups comprise from 1 to 6 carbon atoms.

11. A polymer according to claim 1, wherein said hydrocarbons are chosen from polymethylene groups comprising from 1 to 20 carbon atoms.

12. A polymer according to claim 11, wherein said hydrocarbons are chosen from polymethylene groups from comprising 2 to 8 carbon atoms.

13. A polymer according to claim 1, wherein said monohydroxyalkyl groups are chosen from hydroxymethyl groups, hydroxyethyl groups, hydroxypropyl groups, and hydroxybutyl groups.

14. A polymer according to claim 1, wherein said polyhydroxyalkyl groups are chosen from dihydroxyethyl groups, dihydroxypropyl groups, trihydroxypropyl groups, and dihydroxybutyl groups.

15. A polymer according to claim 1, wherein said cycloalkyl groups are chosen from cyclohexyl groups and cyclopentyl groups.

16. A polymer according to claim 1, wherein said aryl groups are chosen from phenyl groups and naphthyl groups.

17. A polymer according to claim 1, wherein said alkylaryl groups are chosen from benzyl groups, phenethyl groups, and naphthylmethyl groups.

18. A polymer according to claim 1, wherein said at least one 5- to 7-membered aromatic ring is chosen from phenyl groups, pyrimidine groups, pyridine groups, pyrrole groups, and pyrazole groups.

19. A polymer according to claim 1, wherein said inorganic acids are chosen from phosphoric acids and sulphuric acids.

20. A polymer according to claim 1, wherein said organic acids are chosen from sulphonic acids, carboxylic acids, alkanoic acids comprising from 1 to 12 carbon atoms, phenylalkanoic acids, benzoic acids, citric acids, and para-toluenesulphonic acids.

21. A polymer according to claim 1, wherein $X^-$ is chosen from a chloride anion and a bromide anion.

22. A polymer comprising at least one unit of formula (VIII):

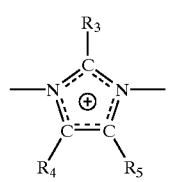

wherein:
$A_1^+$, which may be identical or different, is chosen from quaternary imidazole groups of formula (IV):

wherein:
$R_3$, $R_4$, and $R_5$, which may be identical or different, are each chosen from a hydrogen atom, halogen atoms, hydroxyl groups, nitro groups, cyano groups, mercapto groups, carboxyl groups, alkyl groups, monohydroxyalkyl groups, polyhydroxyalkyl groups, thioalkyl groups, cyanoalkyl groups, alkoxy groups, acyl groups, acetyloxy groups, cycloalkyl groups, aryl groups, alkylaryl groups, and groups having the formula $-NHR_N$, wherein $R_N$ is chosen from a hydrogen atom, alkyl groups, monohydroxyalkyl groups, polyhydroxyalkyl groups, acetyl groups, and ureido groups; and $R_4$ and $R_5$ may optionally also form, together with the atoms to which they are attached, at least one 5- to 7-membered aromatic ring;

$A_2^+$, which may be identical or different, is chosen from quaternary pyrazole groups of formula (V):

wherein:
$R_6$, $R_7$, and $R_8$, which may be identical or different, are each chosen from a hydrogen atom, halogen atoms, hydroxyl groups, nitro groups, cyano groups, mercapto groups, carboxyl groups, alkyl groups, monohydroxyalkyl groups, polyhydroxyalkyl groups, thioalkyl groups, cyanoalkyl groups, alkoxy groups, acyl groups, acetyloxy groups, cycloalkyl groups, aryl groups, alkylaryl groups, and groups having the formula $-NHR_N$, wherein $R_N$ is chosen from a hydrogen atom, alkyl groups, monohydroxyalkyl groups, polyhydroxyalkyl groups, acetyl groups, and ureido groups;

wherein two of said $R_6$, $R_7$, and $R_8$ may optionally also form, together with the atoms to which they are attached, at least one 5- to 7-membered aromatic ring;

$B_1$ and $B_2$, which may be identical or different, are each chosen from hydrocarbons optionally having at least one substituent chosen from optionally substituted aromatic rings, an oxygen atom, a sulphur atom, a nitrogen atom, an $-SO-$ group, an $-SO_2-$ group, an $-SO_3H$ group, amino groups, alkylamino groups, hydroxyl groups, quaternary ammonium groups, and ureido groups, wherein said at least one substituent is bonded to or inserted in the main chain of said polymer; and $X^-$ is chosen from halide anions and anions derived from at least one acid chosen from organic acids and inorganic acids.

23. A polymer according to claim 22, wherein at least one of said $B_1$ and $B_2$, which may be identical or different, is chosen from groups of formula (VI):

$$-(CH_2)_n-CO-A-OC-(CH_2)_n- \quad (VI)$$

wherein:
n is an integer ranging from 1 to 10;
A is chosen from:
(a) glycol residues of formula $-O-Z-O-$ in which Z is chosen from hydrocarbons, and groups having the formula:

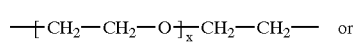 or

-continued

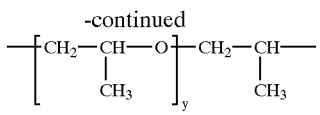

wherein x and y, which may be identical or different, are each a number ranging from 1 to 4;
(b) bis(secondary amine) groups;
(c) bis(primary amine) groups having the formula:

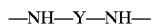

wherein Y is chosen from hydrocarbons, and groups having the formula —$(CH_2)_2$—S—S—$(CH_2)_2$—; and
(d) ureylene groups.

24. A polymer according to claim 23, wherein n is an integer from 1 to 6.

25. A polymer according to claim 22, wherein said $B_1$ and $B_2$, which may be identical or different, are each chosen from:
(a) groups having the formula:

—$(CH_2)_n$— wherein n is an integer ranging from 1 to 6;
(b) groups having the formula:

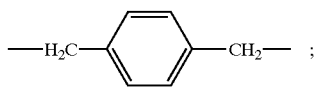

and
(c) groups having the formula:

26. A polymer according to claim 22, wherein said polymer has a mass-average molecular weight ranging from 1000 to 20,000.

27. A polymer according to claim 22, wherein said halogen atoms are chosen from fluorine, chlorine, bromine, and iodine.

28. A polymer according to claim 22, wherein said alkyl groups, said monohydroxyalkyl groups, said polyhydroxyalkyl groups, and said hydrocarbons are each linear, branched or cyclic.

29. A polymer according to claim 22, wherein said alkyl groups comprise from 1 to 20 carbon atoms.

30. A polymer according to claim 29, wherein said alkyl groups are chosen from methyl groups, ethyl groups, propyl groups, isopropyl groups, n-propyl groups, butyl groups, n-butyl groups, tert-butyl groups, pentyl groups, n-pentyl groups, isopentyl groups, n-hexyl groups, isohexyl groups, heptyl groups, octyl groups, nonyl groups, decyl groups, undecyl groups, dodecyl groups, and pentadecyl groups.

31. A polymer according to claim 29, wherein said alkyl groups comprise from 1 to 6 carbon atoms.

32. A polymer according to claim 22, wherein said hydrocarbons are chosen from polymethylene groups comprising from 1 to 20 carbon atoms.

33. A polymer according to claim 32, wherein said hydrocarbons are chosen from polymethylene groups from comprising 2 to 8 carbon atoms.

34. A polymer according to claim 22, wherein said monohydroxyalkyl groups are chosen from hydroxymethyl groups, hydroxyethyl groups, hydroxypropyl groups, and hydroxybutyl groups.

35. A polymer according to claim 22, wherein said polyhydroxyalkyl groups are chosen from dihydroxyethyl groups, dihydroxypropyl groups, trihydroxypropyl groups, and dihydroxybutyl groups.

36. A polymer according to claim 22, wherein said cycloalkyl groups are chosen from cyclohexyl groups and cyclopentyl groups.

37. A polymer according to claim 22, wherein said aryl groups are chosen from phenyl groups and naphthyl groups.

38. A polymer according to claim 22, wherein said alkylaryl groups are chosen from benzyl groups, phenethyl groups, and naphthylmethyl groups.

39. A polymer according to claim 22, wherein said at least one 5- to 7-membered aromatic ring is chosen from phenyl groups, pyrimidine groups, pyridine groups, pyrrole groups, and pyrazole groups.

40. A polymer according to claim 22, wherein said inorganic acids are chosen from phosphoric acids and sulphuric acids.

41. A polymer according to claim 22, wherein said organic acids are chosen from sulphonic acids, carboxylic acids, alkanoic acids comprising from 1 to 12 carbon atoms, phenylalkanoic acids, benzoic acids, citric acids, and para-toluenesulphonic acids.

42. A polymer according to claim 22, wherein $X^-$ is chosen from a chloride anion and a bromide anion.

43. A polymer comprising at least one unit of formula (IX):

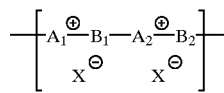

wherein:
$A_1^+$, which may be identical or different, is chosen from:
(a) unsaturated quaternary heterocycles of formula (II):

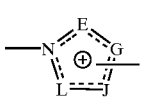

wherein:
E, G, L, and J, which may be identical or different, are each chosen from a carbon atom, an oxygen atom, a sulphur atom, and a nitrogen atom,
wherein at least one of E, G, L, and J is a nitrogen atom;
and further wherein when at least one of E, G, L, and J is a carbon atom, said carbon atom may optionally be substituted by at least one substituent chosen from halogen atoms, hydroxyl groups, nitro groups, cyano groups, mercapto groups, carboxyl groups, alkyl groups, monohydroxyalkyl groups, polyhydroxyalkyl groups, thioalkyl groups, cyanoalkyl groups, alkoxy groups, acyl groups, acetyloxy groups, cycloalkyl groups, optionally substituted, aryl groups, optionally substituted, alkylaryl groups, optionally substituted, and groups having the formula —$NHR_N$ wherein $R_N$ is chosen from a hydrogen atom, alkyl groups, monohydroxyalkyl groups, polyhydroxyalkyl groups, acetyl groups, and ureido groups;

with the proviso that when at least two of said E, G, L, and J are each nitrogen atoms, then at least one of said at least two of said E, G, L, and J may be substituted with a substituent chosen from a hydrogen atom, alkyl groups, monohydroxyalkyl groups, polyhydroxyalkyl groups, aryl groups, optionally substituted, and alkylaryl groups, optionally substituted;

with the further proviso that when at least two of E, G, L, and J are substituted, the substituents may optionally also form, together with the atoms to which they are attached, at least one 5- to 7-membered aromatic ring, optionally substituted; and (b) a quaternary ammonium of formula (III):

$$-\overset{R_1}{\underset{R_2}{N^\oplus}}-\quad (III)$$

wherein:

$R_1$ and $R_2$, which may be identical or different, are each chosen from carboxyl groups, alkyl groups, polyhydroxyalkyl groups, thioalkyl groups, cyanoalkyl groups, alkoxy groups, acyl groups, acetyloxy groups, cycloalkyl groups, optionally substituted, aryl groups, optionally substituted, alkylaryl groups, optionally substituted, and groups having the formula —$NHR_N$ wherein $R_N$ is chosen from a hydrogen atom, alkyl groups, monohydroxyalkyl groups, polyhydroxyalkyl groups, acetyl groups, and ureido groups;

wherein $R_1$ and $R_2$ may optionally also form, together with the nitrogen atom to which they are attached, at least one saturated 5- to 7-membered carbon-based ring;

$A_2^+$, which may be identical or different, is chosen from quaternary imidazole groups of formula (IV):

$$\text{(IV)}$$

wherein:

$R_4$ and $R_5$, which may be identical or different, are each chosen from a hydrogen atom, halogen atoms, hydroxyl groups, nitro groups, cyano groups, mercapto groups, carboxyl groups, alkyl groups, monohydroxyalkyl groups, polyhydroxyalkyl groups, thioalkyl groups, cyanoalkyl groups, alkoxy groups, acyl groups, acetyloxy groups, cycloalkyl groups, aryl groups, alkylaryl groups, groups having the formula —$NHR_N$ in which $R_N$ is chosen from a hydrogen atom, alkyl groups, monohydroxyalkyl groups, polyhydroxyalkyl groups, acetyl groups, and ureido groups;

$R_3$ is chosen from cycloalkyl groups, aryl groups, and alkylaryl groups;

$B_1$ and $B_2$, which may be identical or different, are each chosen from hydrocarbons optionally having at least one substituent chosen from optionally substituted aromatic rings, an oxygen atom, a sulphur atom, a nitrogen atom, an —SO— group, an —$SO_2$— group, an —$SO_3H$ group, amino groups, alkylamino groups, hydroxyl groups, quaternary ammonium groups, and ureido groups, wherein said at least one substituent is bonded to or inserted in the main chain of said polymer; and $X^-$ is chosen from halide anions and anions derived from at least one acid chosen from organic acids and inorganic acids, with the further proviso that if:

(a) $R_4$ and $R_5$ are chosen from a hydrogen atom, $C_1$–$C_{17}$ alkyl groups, and $C_6$–$C_8$ aryl groups;

(b) $R_3$ is chosen from $C_6$–$C_8$ aryl groups; and (c) $A_1^+$ is chosen from unsaturated quaternary heterocycles of formula (II), wherein:

only one of said E, G, L and J is chosen from a nitrogen atom, the others of said E, G, L, and J are chosen from a carbon atom, and G is a nitrogen atom, and E is substituted with at least one substituent chosen from a hydrogen atom, $C_1$–$C_{17}$ alkyl groups and $C_6$–$C_8$ aryl groups, or J is a nitrogen atom, and L is substituted with at least one substituent chosen from a hydrogen atom, $C_1$–$C_{17}$ alkyl groups, and $C_6$–$C_8$ aryl groups, then $B_1$ and $B_2$ are not both chosen from groups having the formula:

$$-H_2C-\langle\text{phenyl}\rangle-CH_2-$$

44. A polymer according to claim 43, wherein $R_3$ is a phenyl group.

45. A polymer according to claim 43, wherein at least one of said $B_1$ and $B_2$, which may be identical or different, is chosen from groups of formula (VI):

$$-(CH_2)_n-CO-A-OC-(CH_2)_n-\quad (VI)$$

wherein:

n is an integer ranging from 1 to 10;

A is chosen from:

(a) glycol residues of formula: —O—Z—O— in which Z is chosen from hydrocarbons, and groups having the formula:

$$-\!\!+\!\!CH_2-CH_2-O\!\!+\!\!_x CH_2-CH_2-\text{ or}$$

$$-\!\!+\!\!CH_2-\underset{CH_3}{CH}-O\!\!+\!\!_y CH_2-\underset{CH_3}{CH}-$$

wherein x and y, which may be identical or different, are each a number ranging from 1 to 4;

(b) bis(secondary amine) groups;

(c) bis(primary amine) groups having the formula:

—NH—Y—NH— wherein Y is chosen from hydrocarbons, and groups having the formula —$(CH_2)_2$—S—S—$(CH_2)_2$—; and (d) ureylene groups.

46. A polymer according to claim 45, wherein n is an integer from 1 to 6.

47. A polymer according to claim 43, wherein said $B_1$ and $B_2$, which may be identical or different, are each chosen from:
(a) groups having the formula:

wherein n is an integer ranging from 1 to 6;
(b) groups having the formula:

and
(c) groups having the formula:

48. A polymer according to claim 43, wherein said polymer has a mass-average molecular weight ranging from 1000 to 20,000.

49. A polymer according to claim 43, wherein said halogen atoms are chosen from fluorine, chlorine, bromine, and iodine.

50. A polymer according to claim 43, wherein said alkyl groups, said monohydroxyalkyl groups, said polyhydroxyalkyl groups, and said hydrocarbons are each linear, branched or cyclic.

51. A polymer according to claim 43, wherein said alkyl groups comprise from 1 to 20 carbon atoms.

52. A polymer according to claim 51, wherein said alkyl groups are chosen from methyl groups, ethyl groups, propyl groups, isopropyl groups, n-propyl groups, butyl groups, n-butyl groups, tert-butyl groups, pentyl groups, n-pentyl groups, isopentyl groups, n-hexyl groups, isohexyl groups, heptyl groups, octyl groups, nonyl groups, decyl groups, undecyl groups, dodecyl groups, and pentadecyl groups.

53. A polymer according to claim 50, wherein said alkyl groups comprise from 1 to 6 carbon atoms.

54. A polymer according to claim 43, wherein said hydrocarbons are chosen from pblymethylene groups comprising from 1 to 20 carbon atoms.

55. A polymer according to claim 54, wherein said hydrocarbons are chosen from polymethylene groups from comprising 2 to 8 carbon atoms.

56. A polymer according to claim 43, wherein said monohydroxyalkyl groups are chosen from hydroxymethyl groups, hydroxyethyl groups, hydroxypropyl groups, and hydroxybutyl groups.

57. A polymer according to claim 43, wherein said polyhydroxyalkyl groups are chosen from dihydroxyethyl groups, dihydroxypropyl groups, trihydroxypropyl groups, and dihydroxybutyl groups.

58. A polymer according to claim 43, wherein said cycloalkyl groups are chosen from cyclohexyl groups and cyclopentyl groups.

59. A polymer according to claim 43, wherein said aryl groups are chosen from phenyl groups and naphthyl groups.

60. A polymer according to claim 43, wherein said alkylaryl groups are chosen from benzyl groups, phenethyl groups, and naphthylmethyl groups.

61. A polymer according to claim 43, wherein said at least one 5- to 7-membered aromatic ring is chosen from phenyl groups, pyrimidine groups, pyridine groups, pyrrole groups, and pyrazole groups.

62. A polymer according to claim 43, wherein said inorganic acids are chosen from phosphoric acids and sulphuric acids.

63. A polymer according to claim 43, wherein said organic acids are chosen from sulphonic acids, carboxylic acids, alkanoic acids comprising from 1 to 12 carbon atoms, phenylalkanoic acids, benzoic acids, citric acids, and para-toluenesulphonic acids.

64. A polymer according to claim 43, wherein $X^-$ is chosen from a chloride anion and a bromide anion.

65. A composition comprising:
(a) at least one agent chosen from:
    (i) reducing agents;
    (ii) oxidizing agents;
    (iii) direct dyes;
    (iv) precursors chosen from oxidation dye precursors and melanin precursors; and
    (v) bleaching agents; and
(b) at least one polymer comprising at least one unit of formula (I):

wherein:
$A_1^+$ and $A_2^+$, which may be identical or different, are each chosen from:
    (a) unsaturated quaternary heterocycles of formula (II):

wherein:
E, G, L, and J, which may be identical or different, are each chosen from a carbon atom, an oxygen atom, a sulphur atom, and a nitrogen atom,
wherein at least one of E, G, L, and J is a nitrogen atom;
and further wherein when at least one of E, G, L, and J is a carbon atom, said carbon atom may optionally be substituted by at least one substituent chosen from halogen atoms, hydroxyl groups, nitro groups, cyano groups, mercapto groups, carboxyl groups, alkyl groups, monohydroxyalkyl groups, polyhydroxyalkyl groups, thioalkyl groups, cyanoalkyl groups, alkoxy groups, acyl groups, acetyloxy groups, cycloalkyl groups, optionally substituted, aryl groups, optionally substituted, alkylaryl groups, optionally substituted, and groups having the formula —$NHR_N$ wherein $R_N$ is chosen from a hydrogen atom, alkyl groups, monohydroxyalkyl groups, polyhydroxyalkyl groups, acetyl groups, and ureido groups;
with the proviso that when at least two of said E, G, L, and J are each nitrogen atoms, then at least one of said at least two of said E, G, L, and J may be substituted with a substituent chosen from a hydrogen atom, alkyl groups, monohydroxyalkyl groups, polyhydroxyalkyl groups, aryl groups, optionally substituted, and alkylaryl groups, optionally substituted;

with the further proviso that when at least two of E, G, L, and J are substituted, the substituents may optionally also form, together with the atoms to which they are attached, at least one 5- to 7-membered aromatic ring, optionally substituted; and (b) quaternary ammoniums of formula (III):

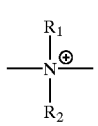

(III)

wherein:
- $R_1$ and $R_2$, which may be identical or different, are each chosen from carboxyl groups, alkyl groups, polyhydroxyalkyl groups, thioalkyl groups, cyanoalkyl groups, alkoxy groups, acyl groups, acetyloxy groups, cycloalkyl groups, optionally substituted, aryl groups, optionally substituted, alkylaryl groups, optionally substituted, and groups having the formula —$NHR_N$ wherein $R_N$ is chosen from a hydrogen atom, alkyl groups, monohydroxyalkyl groups, polyhydroxyalkyl groups, acetyl groups, and ureido groups;
  wherein $R_1$ and $R_2$ may optionally also form, together with the nitrogen atom to which they are attached, at least one saturated 5- to 7-membered carbon-based ring;
  with the proviso that at least one of said $A_1^+$ and said $A_2^+$ is chosen from said unsaturated quaternary heterocycles of formula (II);
- $B_1$ and $B_2$, which may be identical or different, are each chosen from hydrocarbons optionally having at least one substituent chosen from optionally substituted aromatic rings, an oxygen atom, a sulphur atom, a nitrogen atom, an —SO— group, an —$SO_2$— group, an —$SO_3H$ group, amino groups, alkylamino groups, hydroxyl groups, quaternary ammonium groups, and ureido groups, wherein said at least one substituent is bonded to or inserted in the main chain of said polymer; and
- $X^-$ is chosen from halide anions and anions derived from at least one acid chosen from organic acids and inorganic acids.

66. A composition according to claim 65, wherein at least one of said $A_1^+$ and said $A_2^+$ is chosen from unsaturated quaternary heterocycles of formula (II), and wherein said unsaturated quaternary heterocycles of formula (II) are chosen from quaternary imidazole groups of formula (IV):

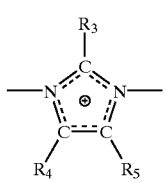

(IV)

wherein:
$R_3$, $R_4$, and $R_5$, which may be identical or different, are each chosen from a hydrogen atom, halogen atoms, hydroxyl groups, nitro groups, cyano groups, mercapto groups, carboxyl groups, alkyl groups, monohydroxyalkyl groups, polyhydroxyalkyl groups, thioalkyl groups, cyanoalkyl groups, alkoxy groups, acyl groups, acetyloxy groups, cycloalkyl groups, aryl groups, alkylaryl groups, and groups having the formula —$NHR_N$ wherein $R_N$ is chosen from a hydrogen atom, alkyl groups, monohydroxyalkyl groups, polyhydroxyalkyl groups, acetyl groups, and ureido groups; and $R_4$ and $R_5$ may optionally also form, together with the atoms to which they are attached, at least one 5- to 7-membered aromatic ring.

67. A composition according to claim 66, wherein both of said $A_1^+$ and said $A_2^+$ are chosen from quaternary imidazole groups of formula (IV), wherein $R_3$, $R_4$, and $R_5$, which may be identical or different, are each chosen from a hydrogen atom, hydroxyl groups, nitro groups, cyano groups, mercapto groups, carboxyl groups, alkyl groups, monohydroxyalkyl groups, and polyhydroxyalkyl groups;
  wherein said $R_4$ and $R_5$ may optionally also form, together with the atoms to which they are attached, at least one 5- to 7-membered aromatic ring.

68. A composition according to claim 66, wherein both of said $A_1^+$ and said $A_2^+$ are chosen from quaternary imidazole groups of formula (IV), wherein $R_3$, $R_4$, and $R_5$, which may be identical or different, are each chosen from a hydrogen atom, and $C_1$ to $C_6$ alkyl groups;
  wherein said $R_4$ and $R_5$ may optionally also form, together with the atoms to which they are attached, at least one phenyl ring.

69. A composition according to claim 65, wherein at least one of said $A_1^+$ and said $A_2^+$ is chosen from unsaturated quaternary heterocycles of formula (II), and wherein said unsaturated quaternary heterocycles of formula (II) are chosen from quaternary pyrazole groups of formula (V):

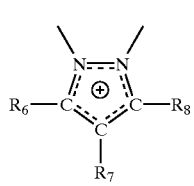

(V)

wherein:
$R_6$, $R_7$, and $R_8$, which may be identical or different, are each chosen from a hydrogen atom, halogen atoms, hydroxyl groups, nitro groups, cyano groups, mercapto groups, carboxyl groups, alkyl groups, monohydroxyalkyl groups, polyhydroxyalkyl groups, thioalkyl groups, cyanoalkyl groups, alkoxy groups, acyl groups, acetyloxy groups, cycloalkyl groups, aryl groups, alkylaryl groups, and groups having the formula —$NHR_N$, wherein $R_N$ is chosen from a hydrogen atom, alkyl groups, monohydroxyalkyl groups, polyhydroxyalkyl groups, acetyl groups, and ureido groups; and wherein two of said $R_6$, $R_7$, and $R_8$ may optionally also form, together with the atoms to which they are attached, at least one 5- to 7-membered aromatic ring.

70. A composition according to claim 65, wherein said $A_1^+$ is chosen from unsaturated quaternary heterocycles of formula (II), and wherein said unsaturated quaternary heterocycles of formula (II) are chosen from quaternary imidazole groups of formula (IV):

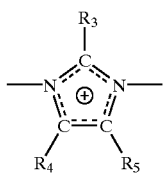
(IV)

wherein:

$R_3$, $R_4$, and $R_5$, which may be identical or different, are each chosen from a hydrogen atom, halogen atoms, hydroxyl groups, nitro groups, cyano groups, mercapto groups, carboxyl groups, alkyl groups, monohydroxyalkyl groups, polyhydroxyalkyl groups, thioalkyl groups, cyanoalkyl groups, alkoxy groups, acyl groups, acetyloxy groups, cycloalkyl groups, aryl groups, alkylaryl groups, and groups having the formula —$NHR_N$ wherein $R_N$ is chosen from a hydrogen atom, alkyl groups, monohydroxyalkyl groups, polyhydroxyalkyl groups, acetyl groups, and ureido groups; and $R_4$ and $R_5$ may optionally also form, together with the atoms to which they are attached, at least one 5- to 7-membered aromatic ring; and further wherein said $A_2^+$ is chosen from unsaturated quaternary heterocycles of formula (II), and wherein said unsaturated quaternary heterocycles of formula (II) are chosen from quaternary pyrazole groups of formula (V):

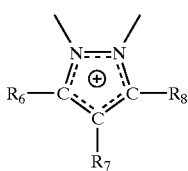
(V)

wherein:

$R_6$, $R_7$, and $R_8$, which may be identical or different, are each chosen from a hydrogen atom, halogen atoms, hydroxyl groups, nitro groups, cyano groups, mercapto groups, carboxyl groups, alkyl groups, monohydroxyalkyl groups, polyhydroxyalkyl groups, thioalkyl groups, cyanoalkyl groups, alkoxy groups, acyl groups, acetyloxy groups, cycloalkyl groups, aryl groups, alkylaryl groups, and groups having the formula —$NHR_N$, wherein $R_N$ is chosen from a hydrogen atom, alkyl groups, monohydroxyalkyl groups, polyhydroxyalkyl groups, acetyl groups, and ureido groups; and wherein two of said $R_6$, $R_7$, and $R_8$ may optionally also form, together with the atoms to which they are attached, at least one 5- to 7-membered aromatic ring.

71. A composition according to claim 65, wherein said $A_1^+$ is chosen from quaternary ammoniums of formula (III), and wherein said $A_2^+$ is chosen from unsaturated quaternary heterocycles of formula (II), and wherein said unsaturated quaternary heterocycles of formula (II) are chosen from quaternary imidazole groups of formula (IV):

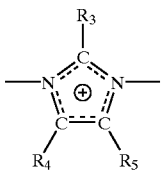
(IV)

wherein:

$R_3$, $R_4$, and $R_5$, which may be identical or different, are each chosen from a hydrogen atom, halogen atoms, hydroxyl groups, nitro groups, cyano groups, mercapto groups, carboxyl groups, alkyl groups, monohydroxyalkyl groups, polyhydroxyalkyl groups, thioalkyl groups, cyanoalkyl groups, alkoxy groups, acyl groups, acetyloxy groups, cycloalkyl groups, aryl groups, alkylaryl groups, and groups having the formula —$NHR_N$ wherein $R_N$ is chosen from a hydrogen atom, alkyl groups, monohydroxyalkyl groups, polyhydroxyalkyl groups, acetyl groups, and ureido groups; and $R_4$ and $R_5$ may optionally also form, together with the atoms to which they are attached, at least one 5- to 7-membered aromiatic ring.

72. A composition according to claim 65, wherein said $A_2^+$ is chosen from unsaturated quaternary heterocycles of formula (II), and wherein said unsaturated quaternary heterocycles of formula (II) are chosen from quaternary imidazole groups of formula (IV):

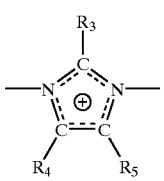
(IV)

wherein:

$R_4$ and $R_5$, which may be identical or different, are each chosen from a hydrogen atom, halogen atoms, hydroxyl groups, nitro groups, cyano groups, mercapto groups, carboxyl groups, alkyl groups, monohydroxyalkyl groups, polyhydroxyalkyl groups, thioalkyl groups, cyanoalkyl groups, alkoxy groups, acyl groups, acetyloxy groups, cycloalkyl groups, aryl groups, alkylaryl groups, groups having the formula —$NHR_N$ in which $R_N$ is chosen from a hydrogen atom, alkyl groups, monohydroxyalkyl groups, polyhydroxyalkyl groups, acetyl groups, and ureido groups; and $R_3$ is chosen from cycloalkyl groups, aryl groups, and alkylaryl groups.

73. A composition according to claim 65, wherein at least one of said $B_1$ and $B_2$, which may be identical or different, is chosen from groups of formula (VI):

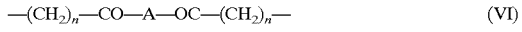
(VI)

wherein:

n is an integer ranging from 1 to 10;

A is chosen from:

(a) glycol residues of formula: —O—Z—O— in which Z is chosen from hydrocarbons, and groups having the formula:

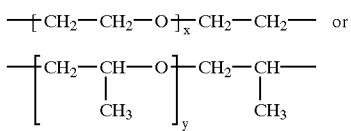

wherein x and y, which may be identical or different, are each a number ranging from 1 to 4;
(b) bis(secondary amine) groups;
(c) bis(primary amine) groups having the formula:

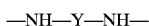

wherein Y is chosen from hydrocarbons, and groups having the formula —$(CH_2)_2$—S—S—$(CH_2)_2$—; and
(d) ureylene groups.

74. A composition according to claim 73, wherein n is an integer from 1 to 6.

75. A composition according to claim 65, wherein said $B_1$ and $B_2$, which may be identical or different, are each chosen from:
(a) groups having the formula:

wherein n is an integer ranging from 1 to 6;
(b) groups having the formula:

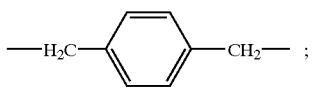

and
(c) groups having the formula:

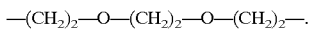

76. A composition according to claim 65, wherein said $X^-$ is chosen from halide anions.

77. A composition according to claim 65, wherein said at least one agent is chosen from reducing agents.

78. A composition according to claim 77, wherein said composition may further comprises a medium appropriate for the permanent shaping of keratinous fibers.

79. A composition according to claim 78, wherein said reducing agents are chosen from sulphites, bisulphites, and thiols.

80. A composition according to claim 79, wherein said reducing agents are chosen from cysteine, cysteamine, and thiolactic acid, thioglycolic acid.

81. A composition according to claim 79, wherein the derivatives of said reducing agents are chosen from salts and esters of said reducing agents.

82. A composition according to claim 77, wherein said reducing agents are present in amount ranging from 1% to 25% by weight, relative to the total weight of said composition.

83. A composition according to claim 82, wherein said reducing agents are present in amount ranging from 1% to 10% by weight, relative to the total weight of said composition.

84. A composition according to claim 77, wherein said composition has a pH ranging from 6.5 to 11.5.

85. A composition according to claim 77, further comprising at least one surface active agent chosen from non-ionic surface active agents, anionic surface active agents, cationic surface active agents, and amphoteric surface active agents.

86. A composition according to claim 85, wherein said at least one surface active agent is chosen from alkyl sulphates, alkylbenzenesulphonates, alkyl ether sulphates, alkylsulphonates, quaternary ammonium salts, alkyl betaines, oxyethylenated alkylphenols, alkylpolyglucosides, fatty acid alkanolamides, oxyethylenated fatty acid esters, and hydroxypropyl ethers.

87. A composition according to claim 86, wherein said at least one surface active agent is present in an amount up to 30% by weight, relative to the total weight of said composition.

88. A composition according to claim 87, wherein said at least one surface active agent is present in an amount ranging from 0.5% to 10% by weight, relative to the total weight of said composition.

89. A composition according to claim 77, further comprising at least one additive chosen from thickening agents, treating agents, waxes, anionic polymers, cationic polymers different from said at least one polymer as defined in claim 39, nonionic polymers, amphoteric polymers, swelling agents, penetrating agents, fatty alcohols, lanolins, ceramides, active ingredients, agents for combating hair loss, antidandruff agents, suspending agents, sequestering agents, opacifying agents, dyes, silicone-comprising sunscreens, non-silicone-comprising sunscreens, fragrances, and preservatives.

90. A composition according to claim 89, wherein said thickening agents are chosen from guar gums, tara gums, and spruce flours.

91. A composition according to claim 89, wherein said treating agents are chosen from volatile and non-volatile, linear, branched, and cyclic silicones.

92. A composition according to claim 89, wherein said active ingredients are chosen from pantothenic acid and panthenol.

93. A composition according to claim 65, wherein said at least one polymer comprising at least one unit of formula (I) is present in amount ranging from 0.01% to 10% by weight, relative to the total weight of said composition.

94. A composition according to claim 93, wherein said at least one polymer comprising at least one unit of formula (I) is present in amount ranging from 1% to 5% by weight, relative to the total weight of said composition.

95. A composition according to claim 65, wherein said at least one agent is chosen from oxidizing agents.

96. A composition according to claim 95, further comprising a medium appropriate for the permanent shaping of keratin fibers.

97. A composition according to claim 95, wherein said oxidizing agents are chosen from aqueous hydrogen peroxide solution, urea hydrogen peroxide, bromates, persalts, and enzymes.

98. A composition according to claim 95, wherein said composition has a pH ranging from 2 to 9.

99. A composition according to claim 98, wherein said composition has a pH ranging from 3 to 8.

100. A composition according to claim 65, wherein said at least one agent is chosen from direct dyes.

101. A composition according to claim 100, further comprising a medium appropriate for dyeing keratin fibers.

102. A composition according to claim 100, wherein said direct dyes are chosen from azo dyes, anthraquinone dyes, nitrobenzene dyes, triarylmethane dyes, azine dyes, acridine dyes, xanthene dyes, and metalliferous dyes.

103. A composition according to claim 102, wherein said nitrobenzene dyes are chosen from nitrophenylenediamines, nitrodiphenylamines, nitroanilines, nitrophenol ethers, nitrophenols, and nitropyridines.

104. A composition according to claim 102, wherein said azo dyes are chosen from monoazo dyes and diazo dyes.

105. A composition according to claim 102, wherein said direct dyes are chosen from:

i) nitrobenzene dyes of formula (A) and the cosmetically acceptable salts thereof:

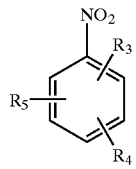

(A)

wherein:
- $R_3$ is chosen from $NH_2$ groups, amino groups monosubstituted with a group chosen from alkyl groups, monohydroxyalkyl groups, polyhydroxyalkyl groups, and aminoalkyl groups, and amino groups disubstituted with two groups, which may be identical or different, each chosen from alkyl groups, monohydroxyalkyl groups, polyhydroxyalkyl groups, and aminoalkyl groups;
- $R_4$ is chosen from a hydrogen atom, hydroxyl groups, alkoxy groups, monohydroxyalkyloxy groups, polyhydroxyalkyloxy groups, $NH_2$ groups, and amino groups monosubstituted with a group chosen from alkyl groups, monohydroxyalkyl groups, polyhydroxyalkyl groups, and aminoalkyl groups; and
- $R_5$ is chosen from a hydrogen atom, alkyl groups, nitro groups, and halogen atoms;
- wherein said alkyl groups are chosen from linear, branched, and cyclic $C_1$ to $C_4$ alkyl groups, and
- wherein said alkoxy groups are chosen from linear, branched, and cyclic $C_1$ to $C_4$ alkoxy groups;

ii) anthraquinone dyes of formula (B) and the cosmetically acceptable salts thereof:

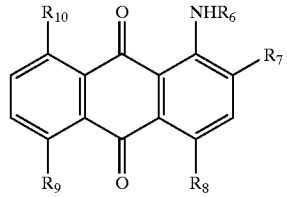

(B)

wherein:
- $R_6$ is chosen from a hydrogen atom, monohydroxyalkyl groups, and polyhydroxyalkyl groups;
- $R_7$ is chosen from a hydrogen atom, alkyl groups, and alkoxy groups;
- $R_8$ is chosen from a hydrogen atom, hydroxyl groups, amino groups, monohydroxyalkylamino groups, and polyhydroxyalkylamino groups; and
- $R_9$ and $R_{10}$, which may be identical or different, are each chosen from a hydrogen atom, hydroxyl groups, and amino groups;
- wherein said alkyl groups are chosen from linear, branched, and cyclic $C_1$ to $C_4$ alkyl groups, and wherein said alkoxy groups are chosen from linear, branched, and cyclic $C_1$ to $C_4$ alkoxy groups; and iii) azo dyes of formula (C) and the cosmetically acceptable salts thereof:

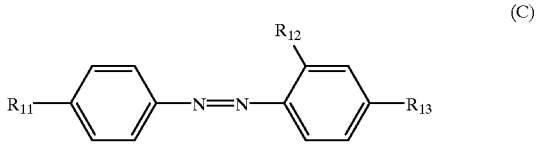

(C)

wherein:
- $R_{11}$ is chosen from nitro groups, amino groups, monoalkyl amino groups, and dialkyl amino groups;
- $R_{12}$ is chosen from a hydrogen atom and alkyl groups;
- $R_{13}$ is chosen amino groups, optionally substituted with at least one monohydroxyalkyl group;
- wherein said alkyl groups are chosen from linear, branched, and cyclic $C_1$ to $C_4$ alkyl groups; and
- wherein said alkoxy groups are chosen from linear, branched, and cyclic $C_1$ to $C_4$ alkoxy groups.

106. A composition according to claim 103, herein said direct dyes are chosen from:
- 1-amino-2-nitro-4-N-(β-hydroxyethyl)amino-5-methylbenzene;
- 1,4,5,8-tetraaminoanthraquinone;
- 1,4-bis-N,N'-[(β,γ-dihydroxypropyl)amino]-anthraquinone;
- 1,4,4-N-tris(β-hydroxyethyl)-1,4-diamino-2-nitrobenzene;
- 1-N-(β-hydroxyethyl)amino-2-nitro-4-aminobenzene;
- 1-hydroxy-3-nitro-4-aminobenzene;
- 1-hydroxy-3-nitro-4-N-(β-hydroxyethyl)aminobenzene;
- 1-(β-hydroxyethyloxy)-3-methylamino-4-nitrobenzene;
- 1-methylamino-2-nitro-5-(β,γ-dihydroxypropyloxy)benzene;
- 1-N-(β-aminoethyl)amino-2-nitro-4-(β-hydroxyethyloxy)benzene;
- 4-[N-ethyl-N-(β-hydroxyethyl)amino]-1-N-(β-hydroxyethyl)amino-2-nitrobenzene;
- 1-(4'-aminodiphenylazo)-2-methyl-4-N-bis(β-hydroxyethyl)aminobenzene;
- 1-methoxy-3-N-(β-aminoethyl)amino-4-nitrobenzene;
- 1-amino-2-nitro-4-N-(β-hydroxyethyl)aminobenzene;
- 1-amino-2-nitro-4-N-bis(β-hydroxyethyl)aminobenzene;
- 1,4-N-bis(β-hydroxyethyl)amino-5-nitrobenzene;
- 1,4-diaminoanthraquinone; and
- cosmetically acceptable salts thereof.

107. A composition according to claim 100, wherein said direct dyes are present in an amount ranging from 0.001% to 10% by weight, relative to the total weight of said composition.

108. A composition according to claim 107, wherein said direct dyes are present in an amount ranging from 0.05% to 5% by weight, relative to the total weight of said composition.

109. A composition according to claim 65, wherein said at least one agent is chosen from precursors.

110. A composition according to claim 109, further comprising a medium appropriate for dyeing keratin fibers.

111. A composition according to claim 65, wherein said oxidation dye precursors are chosen from para-phenylenediamines, para-aminophenols, ortho-phenylenediamines, heterocyclic bases and acid addition salts thereof.

112. A composition according to claim 65, wherein said oxidation dye precursors, if present, are present in an amount ranging from 0.0005% to 12% by weight, relative to the total weight of said composition.

113. A composition according to claim 109, further comprising at least one coupler.

114. A composition according to claim 113, wherein said at least one coupler is chosen from meta-phenylenediamines, meta-aminophenols, meta-diphenols, heterocyclic couplers, and the acid addition salts of said meta-phenylenediamines, meta-aminophenols, meta-diphenols, and heterocyclic couplers.

115. A composition according to claim 113, wherein said at least one coupler is present in an amount ranging from 0.0001% to 10% by weight, relative to the total weight of said composition.

116. A composition according to claim 110, wherein said medium appropriate for dyeing is present in amount ranging from 1% to 40% by weight of the total weight of said composition.

117. A composition according to claim 116, wherein said medium appropriate for dyeing is present in amount ranging from 5% to 30% by weight of the total weight of said composition.

118. A composition according to claim 109, wherein said composition has a pH ranging from 3 to 12.

119. A composition according to claim 118, wherein said composition has a pH ranging from 5 to 11.

120. A composition according to claim 65, wherein said at least one agent is chosen from bleaching agents.

121. A composition according to claim 120, further comprising a medium appropriate for bleaching for keratinous fibers.

122. A composition according to claim 120, wherein said bleaching agents are chosen from hydrogen peroxide, persulphates, percarbonates, and perborates.

123. A process for dyeing at least one keratinous fiber comprising:

(a) applying an effective amount of a composition to said at least one keratinous fiber for a time sufficient to achieve a desired coloration in an amount sufficient to achieve said desired coloration, and (b) rinsing said at least one keratinous fiber; wherein said composition comprises:

(i) at least one agent chosen from oxidation dye precursors, melanin precursors, oxidizing agents and direct dyes; and (ii) at least one polymer comprising at least one unit of formula (I):

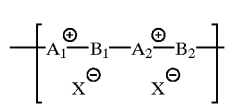

(I)

wherein:

$A_1^+$ and $A_2^+$, which may be identical or different, are each chosen from:

(a) unsaturated quaternary heterocycles of formula (II):

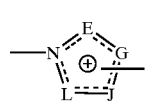

(II)

wherein:

E, G, L, and J, which may be identical or different, are each chosen from a carbon atom, an oxygen atom, a sulphur atom, and a nitrogen atom, wherein at least one of E, G, L, and J is a nitrogen atom;

and further wherein when at least one of E, G, L, and J is a carbon atom, said carbon atom may optionally be substituted by at least one substituent chosen from halogen atoms, hydroxyl groups, nitro groups, cyano groups, mercapto groups, carboxyl groups, alkyl groups, monohydroxyalkyl groups, polyhydroxyalkyl groups, thioalkyl groups, cyanoalkyl groups, alkoxy groups, acyl groups, acetyloxy groups, cycloalkyl groups, optionally substituted, aryl groups, optionally substituted, alkylaryl groups, optionally substituted, and groups having the formula —$NHR_N$ wherein $R_N$ is chosen from a hydrogen atom, alkyl groups, monohydroxyalkyl groups, polyhydroxyalkyl groups, acetyl groups, and ureido groups;

with the proviso that when at least two of said E, G, L, and J are each nitrogen atoms, then at least one of said at least two of said E, G, L, and J may be substituted with a substituent chosen from a hydrogen atom, alkyl groups, monohydroxyalkyl groups, polyhydroxyalkyl groups, aryl groups, optionally substituted, and alkylaryl groups, optionally substituted;

with the further proviso that when at least two of E, G, L, and J are substituted, the substituents may optionally also form, together with the atoms to which they are attached, at least one 5- to 7-membered aromatic ring, optionally substituted; and (b) quaternary ammoniums of formula (III):

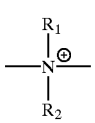

(III)

wherein:

$R_1$ and $R_2$, which may be identical or different, are each chosen from carboxyl groups, alkyl groups, polyhydroxyalkyl groups, thioalkyl groups, cyanoalkyl groups, alkoxy groups, acyl groups, acetyloxy groups, cycloalkyl groups, optionally substituted, aryl groups, optionally substituted, alkylaryl groups, optionally substituted, and groups having the formula —$NHR_N$ wherein $R_N$ is chosen from a hydrogen atom, alkyl groups, monohydroxyalkyl groups, polyhydroxyalkyl groups, acetyl groups, and ureido groups;

wherein $R_1$ and $R_2$ may optionally also form, together with the nitrogen atom to which they are attached, at least one saturated 5- to 7-membered carbon-based ring;

with the proviso that at least one of said $A_1^+$ and said $A_2^+$ is chosen from said unsaturated quaternary heterocycles of formula (II);

$B_1$ and $B_2$, which may be identical or different, are each chosen from hydrocarbons optionally having at least one substituent chosen from optionally substituted aromatic rings, an oxygen atom, a sulphur atom, a nitrogen atom, an —SO— group, an —SO$_2$— group, an —SO$_3$H group, amino groups, alkylamino groups, hydroxyl groups, quaternary ammonium groups, and ureido groups wherein said at least one substituent is bonded to or inserted in the main chain of said polymer; and $X^-$ is chosen from halide anions and anions derived from at least one acid chosen from organic acids and inorganic acids.

124. A process according to claim 123, wherein said time sufficient to achieve a desired coloration ranges from 10 to 60 minutes.

125. A process according to claim 123, wherein said time sufficient to achieve a desired coloration ranges from 5 to 45 minutes.

126. A process according to claim 123, wherein at least one of said $A_1^+$ and said $A_2^+$ is chosen from unsaturated quaternary heterocycles of formula (II), and wherein said unsaturated quaternary heterocycles of formula (II) are chosen from quaternary imidazole groups of formula (IV):

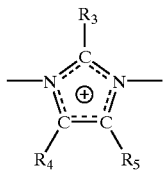

(IV)

wherein $R_3$, $R_4$, and $R_5$, which may be identical or different, are each chosen from a hydrogen atom, halogen atoms, hydroxyl groups, nitro groups, cyano groups, mercapto groups, carboxyl groups, alkyl groups, monohydroxyalkyl groups, polyhydroxyalkyl groups, thioalkyl groups, cyanoalkyl groups, alkoxy groups, acyl groups, acetyloxy groups, cycloalkyl groups, aryl groups, alkylaryl groups, and groups having the formula —NHR$_N$, wherein R$_N$ is chosen from a hydrogen atom, alkyl groups, monohydroxyalkyl groups, polyhydroxyalkyl groups, acetyl groups, and ureido groups; and $R_4$ and $R_5$ may optionally also form, together with the atoms to which they are attached, at least one 5- to 7-membered aromatic ring.

127. A process according to claim 126, wherein both of said $A_1^+$ and said $A_2^+$ are chosen from quaternary imidazole groups of formula (IV), wherein $R_3$, $R_4$, and $R_5$, which may be identical or different, are each chosen from a hydrogen atom, hydroxyl groups, nitro groups, cyano groups, mercapto groups, carboxyl groups, alkyl groups, monohydroxyalkyl groups, and polyhydroxyalkyl groups;

wherein said $R_4$ and $R_5$ may optionally also form, together with the atoms to which they are attached, at least one 5- to 7-membered aromatic ring.

128. A process according to claim 126, wherein both of said $A_1^+$ and said $A_2^+$ are chosen from quaternary imidazole groups of formula (IV):

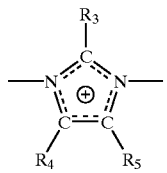

(IV)

wherein $R_3$, $R_4$, and $R_5$, which may be identical or different, are each chosen from a hydrogen atom, and $C_1$ to $C_6$ alkyl groups; and wherein said $R_4$ and $R_5$ may optionally also form, together with the atoms to which they are attached, at least one phenyl ring.

129. A process according to claim 123, wherein at least one of said $A_1^+$ and said $A_2^+$ is chosen from unsaturated quaternary heterocycles of formula (II), and wherein said unsaturated quaternary heterocycles of formula (II) are chosen from quaternary pyrazole groups of formula (V):

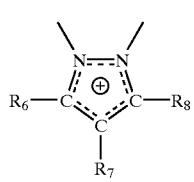

(V)

wherein:

$R_6$, $R_7$, and $R_8$, which may be identical or different, are each chosen from a hydrogen atom, halogen atoms, hydroxyl groups, nitro groups, cyano groups, mercapto groups, carboxyl groups, alkyl groups, monohydroxyalkyl groups, polyhydroxyalkyl groups, thioalkyl groups, cyanoalkyl groups, alkoxy groups, acyl groups, acetyloxy groups, cycloalkyl groups, aryl groups, alkylaryl groups, and groups having the formula —NHR$_N$, wherein R$_N$ is chosen from a hydrogen atom, alkyl groups, monohydroxyalkyl groups, polyhydroxyalkyl groups, acetyl groups, and ureido groups; and wherein two of said $R_6$, $R_7$, and $R_8$ may optionally also form, together with the atoms to which they are attached, at least one 5- to 7-membered aromatic ring.

130. A process according to claim 123, wherein said $A_1^+$ is chosen from unsaturated quaternary heterocycles of formula (II), and wherein said unsaturated quaternary heterocycles of formula (II) are chosen from quaternary imidazole groups of formula (IV):

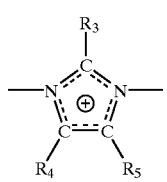

(IV)

wherein:

$R_3$, $R_4$, and $R_5$, which may be identical or different, are each chosen from a hydrogen atom, halogen atoms, hydroxyl groups, nitro groups, cyano groups, mercapto groups, carboxyl groups, alkyl groups, monohydroxyalkyl groups, polyhydroxyalkyl groups, thioalkyl groups, cyanoalkyl groups, alkoxy groups, acyl groups, acetyloxy groups, cycloalkyl groups, aryl groups, alkylaryl groups, and groups having the formula —NHR$_N$ wherein R$_N$ is chosen from a hydrogen atom, alkyl groups, monohydroxyalkyl groups, polyhydroxyalkyl groups, acetyl groups, and ureido groups; and R$_4$ and R$_5$ may optionally also form, together with the atoms to which they are attached, at least one 5- to 7-membered aromatic ring; and further wherein said A$_2^+$ is chosen from unsaturated quaternary heterocycles of formula (II), and wherein said unsaturated quaternary heterocycles of formula (II) are chosen from quaternary pyrazole groups of formula (V):

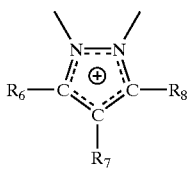

(V)

wherein:

R$_6$, R$_7$, and R$_8$, which may be identical or different, are each chosen from a hydrogen atom, halogen atoms, hydroxyl groups, nitro groups, cyano groups, mercapto groups, carboxyl groups, alkyl groups, monohydroxyalkyl groups, polyhydroxyalkyl groups, thioalkyl groups, cyanoalkyl groups, alkoxy groups, acyl groups, acetyloxy groups, cycloalkyl groups, aryl groups, alkylaryl groups, and groups having the formula —NHR$_N$, wherein R$_N$ is chosen from a hydrogen atom, alkyl groups, monohydroxyalkyl groups, polyhydroxyalkyl groups, acetyl groups, and ureido groups; and wherein two of said R$_6$, R$_7$, and R$_8$ may optionally also form, together with the atoms to which they are attached, at least one 5- to 7-membered aromatic ring.

131. A process according to claim 123, wherein said A$_1^+$ is chosen from quaternary ammoniums of formula (III), and wherein said A$_2^+$ is chosen from unsaturated quaternary heterocycles of formula (II), and wherein said unsaturated quaternary heterocycles of formula (II) are chosen from quaternary imidazole groups of formula (IV):

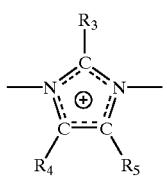

(IV)

wherein:

R$_3$, R$_4$, and R$_5$, which may be identical or different, are each chosen from a hydrogen atom, halogen atoms, hydroxyl groups, nitro groups, cyano groups, mercapto groups, carboxyl groups, alkyl groups, monohydroxyalkyl groups, polyhydroxyalkyl groups, thioalkyl groups, cyanoalkyl groups, alkoxy groups, acyl groups, acetyloxy groups, cycloalkyl groups, aryl groups, alkylaryl groups, and groups having the formula —NHR$_N$ wherein R$_N$ is chosen from a hydrogen atom, alkyl groups, monohydroxyalkyl groups, polyhydroxyalkyl groups, acetyl groups, and ureido groups; and R$_4$ and R$_5$ may optionally also form, together with the atoms to which they are attached, at least one 5- to 7-membered aromatic ring.

132. A process according to claim 123, wherein said A$_2^+$ is chosen from unsaturated quaternary heterocycles of formula (II), and wherein said unsaturated quaternary heterocycles of formula (II) are chosen from quaternary imidazole groups of formula (IV):

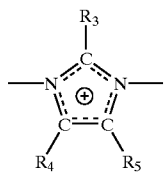

(IV)

wherein:

R$_4$ and R$_5$, which may be identical or different, are each chosen from a hydrogen atom, halogen atoms, hydroxyl groups, nitro groups, cyano groups, mercapto groups, carboxyl groups, alkyl groups, monohydroxyalkyl groups, polyhydroxyalkyl groups, thioalkyl groups, cyanoalkyl groups, alkoxy groups, acyl groups, acetyloxy groups, cycloalkyl groups, aryl groups, alkylaryl groups, groups having the formula —NHR$_N$ in which R$_N$ is chosen from a hydrogen atom, alkyl groups, monohydroxyalkyl groups, polyhydroxyalkyl groups, acetyl groups, and ureido groups; and R$_3$ is chosen from cycloalkyl groups, aryl groups, and alkylaryl groups.

133. A process according to claim 123, wherein at least one of said B$_1$ and B$_2$, which may be identical or different, is chosen from groups of formula (VI):

—(CH$_2$)$_n$—CO—A—OC—(CH$_2$)$_n$— (VI)

wherein:

n is an integer ranging from 1 to 10;

A is chosen from:

(a) glycol residues of formula: —O—Z—O— in which Z is chosen from hydrocarbons, and groups having the formula:

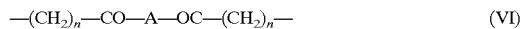 or

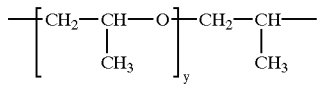

wherein x and y, which may be identical or different, are each a number ranging from 1 to 4;

(b) bis(secondary amine) groups;

(c) bis(primary amine) groups having the formula:

—NH—Y—NH— wherein Y is chosen from hydrocarbons, and groups having the formula —(CH$_2$)$_2$—S—S—(CH$_2$)$_2$—; and (d) ureylene groups.

134. A process according to claim 123, wherein n is an integer from 1 to 6.

135. A process according to claim 123, wherein said B$_1$ and B$_2$, which may be identical or different, are each chosen from:

(a) groups having the formula:

—(CH$_2$)$_n$— wherein n is an integer ranging from 1 to 6;

(b) groups having the formula:

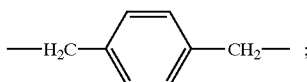

and (c) groups having the formula:

136. A process according to claim 123, wherein said X⁻ is chosen from halide anions.

137. A process according to claim 123, wherein said composition further comprises a medium appropriate for dyeing keratin fibers.

138. A process according to claim 123, wherein said at least one agent is chosen from precursors.

139. A process according to claim 123, wherein said oxidation dye precursors are chosen from para-phenylenediamines, para-aminophenols, ortho-phenylenediamines, heterocyclic bases, and acid addition salts thereof.

140. A process according to claim 139, wherein said acid addition salts are chosen from hydrochlorides, hydrobromides, sulphates, citrates, succinates, tartrates, lactates, and acetates.

141. A process according to claim 139, wherein said heterocyclic bases are chosen from pyridines, pyrimidines, pyrazoles, pyrazolopyrimidines, indoles, and indolines.

142. A process according to claim 123, wherein said oxidation dye precursors, if present, are present in an amount ranging from 0.0005% to 12% by weight, relative to the total weight of said composition.

143. A process according to claim 138, wherein said composition further comprises at least one coupler.

144. A process according to claim 143, wherein said at least one coupler is chosen from meta-phenylenediamines, meta-aminophenols, meta-diphenols, heterocyclic couplers, and acid addition salts thereof.

145. A process according to claim 144, wherein said acid addition salts are chosen from hydrochlorides, hydrobromides, sulphates, citrates, succinates, tartrates, lactates, and acetates.

146. A process according to claim 144, wherein said heterocyclic couplers are chosen from indoles, indolines, benzimidazoles, benzomorpholines, sesamols, pyridines, pyrimidines, and pyrazoles.

147. A process according to claim 143, wherein said at least one coupler is present in an amount ranging from 0.0001% to 10% by weight, relative to the total weight of said composition.

148. A process according to claim 137, wherein said medium appropriate for dyeing keratin fibers is present in amount ranging from 1% to 40% by weight, relative to the total weight of said composition.

149. A process according to claim 145, wherein said medium appropriate for dyeing keratin fibers is present in amount ranging from 5% to 30% by weight, relative to the total weight of said composition.

150. A process according to claim 123, wherein said composition has a pH ranging from 3 to 12.

151. A process according to claim 150, wherein said composition has a pH ranging from 5 to 11.

152. A process according to claim 123, wherein said at least one agent is chosen from oxidizing agents.

153. A process according to claim 152, wherein said oxidizing agents are chosen from aqueous hydrogen peroxide solution, urea hydrogen peroxide, bromates, persalts, and enzymes.

154. A process according to claim 153, wherein said bromates are chosen from alkaline bromates.

155. A process according to claim 152, wherein said enzymes are chosen from peroxidases and two-electron oxidoreductases.

156. A process according to claim 123, wherein said at least one agent is chosen from direct dyes.

157. A process according to claim 156, wherein said direct dyes are chosen from azo dyes, anthraquinone dyes, nitrobenzene dyes, triarylmethane dyes, azine dyes, acridine dyes, xanthene dyes, and metalliferous dyes.

158. A process according to claim 157, wherein said nitrobenzene dyes are chosen from nitrophenylenediamines, nitrodiphenylamines, nitroanilines, nitrophenol ethers, nitrophenols, and nitropyridines.

159. A process according to claim 157, wherein said azo dyes are chosen from monoazo dyes and diazo dyes.

160. A process according to claim 157, wherein said direct dyes are chosen from:

i) nitrobenzene dyes of formula (A) and the cosmetically acceptable salts thereof:

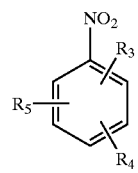

(A)

wherein:

R₃ is chosen from NH₂ groups, amino groups monosubstituted with a group chosen from alkyl groups, monohydroxyalkyl groups, polyhydroxyalkyl groups, and aminoalkyl groups, and amino groups disubstituted with two groups, which may be identical or different, each chosen from alkyl groups, monohydroxyalkyl groups, polyhydroxyalkyl groups, and aminoalkyl groups;

R₄ is chosen from a hydrogen atom, hydroxyl groups, alkoxy groups, monohydroxyalkyloxy groups, polyhydroxyalkyloxy groups, NH₂ groups, and amino groups monosubstituted with a group chosen from alkyl groups, monohydroxyalkyl groups, polyhydroxyalkyl groups, and aminoalkyl groups; and R₅ is chosen from a hydrogen atom, alkyl groups, nitro groups, and halogen atoms;

wherein said alkyl groups are chosen from linear, branched, and cyclic C₁ to C₄ alkyl groups, and wherein said alkoxy groups are chosen from linear, branched, and cyclic C₁ to C₄ alkoxy groups;

ii) anthraquinone dyes of formula (B) and the cosmetically acceptable salts thereof:

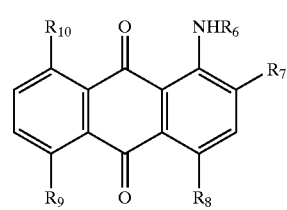

(B)

wherein:

R₆ is chosen from a hydrogen atom, monohydroxyalkyl groups, and polyhydroxyalkyl groups;

R$_7$ is chosen from a hydrogen atom, alkyl groups, and alkoxy groups;

R$_8$ is chosen from a hydrogen atom, hydroxyl groups, amino groups, monohydroxyalkylamino groups, and polyhydroxyalkylamino groups; and R$_9$ and R$_{10}$, which may be identical or different, are each chosen from a hydrogen atom, hydroxyl groups, and amino groups;

wherein said alkyl groups are chosen from linear, branched, and cyclic C$_1$ to C$_4$ alkyl groups, and wherein said alkoxy groups are chosen from linear, branched, and cyclic C$_1$ to C$_4$ alkoxy groups; and iii) azo dyes of formula (C) and the cosmetically acceptable salts thereof:

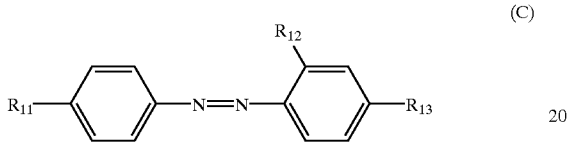

(C)

wherein:

R$_1$ is chosen from nitro groups, amino groups, monoalkyl amino groups, and dialkyl amino groups;

R$_{12}$ is chosen from a hydrogen atom, and alkyl groups;

R$_{13}$ is chosen amino groups, optionally substituted with at least one monohydroxyalkyl group;

wherein said alkyl groups are chosen from linear, branched, and cyclic C$_1$ to C$_4$ alkyl groups; and wherein said alkoxy groups are chosen from linear, branched, and cyclic C$_1$ to C$_4$ alkoxy groups.

161. A process according to claim 156, wherein said at least one direct dye is chosen from:

1-amino-2-nitro-4-N-(β-hydroxyethyl)amino-5-methylbenzene;

1,4,5,8-tetraaminoanthraquinone;

1,4-bis-N,N'-[(β,y-dihydroxypropyl)amino]-anthraquinone;

1,4,4-N-tris(β-hydroxyethyl)-1,4-diamino-2-nitrobenzene;

1-N-(β-hydroxyethyl)amino-2-nitro-4-aminobenzene;

1-hydroxy-3-nitro-4-aminobenzene;

1-hydroxy-3-nitro-4-N-(β-hydroxyethyl)aminobenzene;

1-(β-hydroxyethyloxy)-3-methylamino-4-nitrobenzene;

1-methylamino-2-nitro-5-(β,y-dihydroxypropyloxy) benzene;

1-N-(β-aminoethyl)amino-2-nitro-4-(β-hydroxyethyloxy)benzene;

4-[N-ethyl-N-(β-hydroxyethyl)amino]-1-N-(β-hydroxyethyl)amino-2-nitrobenzene;

1-(4'-aminodiphenylazo)-2-methyl-4-N-bis(β-hydroxyethyl)aminobenzene;

1-methoxy-3-N-(β-aminoethyl)amino-4-nitrobenzene;

1-amino-2-nitro-4-N-(β-hydroxyethyl)aminobenzene;

1-amino-2-nitro-4-N-bis(β-hydroxyethyl)aminobenzene;

1,4-N-bis(β-hydroxyethyl)amino-5-nitrobenzene;

1,4-diaminoanthraquinone; and cosmetically acceptable salts thereof.

162. A process according to claim 156, wherein said direct dyes are present in an amount ranging from 0.001% to 10% by weight, relative to the total weight of said composition.

163. A process according to claim 162, wherein said direct dyes are present in an amount ranging from 0.05% to 5% by weight, relative to the total weight of said composition.

164. A process according to claim 123, wherein said at least one polymer comprising at least one unit of formula (I) is present in an amount ranging from 0.01% to 10% by weight, relative to the total weight of said composition.

165. A process according to claim 164, wherein said at least one polymer comprising at least one unit of formula (I) is present in an amount ranging from 0.1% to 5% by weight, relative to the total weight of said composition.

166. A process for bleaching at least one keratinous fiber comprising:

(a) applying an effective amount of a composition to said at least one keratinous fiber for a time sufficient to bleach said at least one keratinous fiber in an amount sufficient to bleach said at least one keratinous fiber; and (b) rinsing said at least one keratinous fiber; wherein said composition comprises:

(i) at least one bleaching agent; and (ii) at least one polymer comprising at least one unit of formula (I):

(I)

wherein:

A$_1$$^+$ and A$_2$$^+$, which may be identical or different, are each chosen from:

(a) unsaturated quaternary heterocycles of formula (II):

(II)

wherein:

E, G, L, and J, which may be identical or different, are each chosen from a carbon atom, an oxygen atom, a sulphur atom, and a nitrogen atom, wherein at least one of E, G, L, and J is a nitrogen atom;

and further wherein when at least one of E, G, L, and J is a carbon atom, said carbon atom may optionally be substituted by at least one substituent chosen from halogen atoms, hydroxyl groups, nitro groups, cyano groups, mercapto groups, carboxyl groups, alkyl groups, monohydroxyalkyl groups, polyhydroxyalkyl groups, thioalkyl groups, cyanoalkyl groups, alkoxy groups, acyl groups, acetyloxy groups, cycloalkyl groups, optionally substituted, aryl groups, optionally substituted, alkylaryl groups, optionally substituted, and groups having the formula —NHR$_N$ wherein R$_N$ is chosen from a hydrogen atom, alkyl groups, monohydroxyalkyl groups, polyhydroxyalkyl groups, acetyl groups, and ureido groups;

with the proviso that when at least two of said E, G, L, and J are each nitrogen atoms, then at least one of said at least two of said E, G, L, and J may be substituted with a substituent chosen from a hydrogen atom, alkyl groups, monohydroxyalkyl groups, polyhydroxyalkyl groups, aryl groups, optionally substituted, and alkylaryl groups, optionally substituted;

with the further proviso that when at least two of E, G, L, and J are substituted, the substituents may optionally also form, together with the atoms to which they are attached, at least one 5- to 7-membered aromatic ring, optionally substituted; and (b) quaternary ammoniums of formula (III):

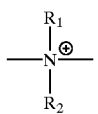

(III)

wherein:

R₁ and R₂, which may be identical or different, are each chosen from carboxyl groups, alkyl groups, polyhydroxyalkyl groups, thioalkyl groups, cyanoalkyl groups, alkoxy groups, acyl groups, acetyloxy groups, cycloalkyl groups, optionally substituted, aryl groups, optionally substituted, alkylaryl groups, optionally substituted, and groups having the formula —NHR$_N$ wherein R$_N$ is chosen from a hydrogen atom, alkyl groups, monohydroxyalkyl groups, polyhydroxyalkyl groups, acetyl groups, and ureido groups;

wherein R₁ and R₂ may optionally also form, together with the nitrogen atom to which they are attached, at least one saturated 5- to 7-membered carbon-based ring;

with the proviso that at least one of said A₁⁺ and said A₂⁺ is chosen from said unsaturated quaternary heterocycles of formula (II);

B₁ and B₂, which may be identical or different, are each chosen from hydrocarbons optionally having at least one substituent chosen from optionally substituted aromatic rings, an oxygen atom, a sulphur atom, a nitrogen atom, an —SO— group, an —SO₂— group, an —SO₃H group, amino groups, alkylamino groups, hydroxyl groups, quaternary ammonium groups, and ureido groups wherein said at least one substituent is bonded to or inserted in the main chain of said polymer; and X⁻ is chosen from halide anions and anions derived from at least one acid chosen from organic acids and inorganic acids.

167. A process according to claim 166, wherein at least one of said A₁⁺ and said A₂⁺ is chosen from unsaturated quaternary heterocycles of formula (II), and wherein said unsaturated quaternary heterocycles of formula (II) are chosen from quaternary imidazole groups of formula (IV):

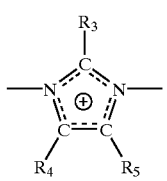

(IV)

wherein:

R₃, R₄, and R₅, which may be identical or different, are each chosen from a hydrogen atom, halogen atoms, hydroxyl groups, nitro groups, cyano groups, mercapto groups, carboxyl groups, alkyl groups, monohydroxyalkyl groups, polyhydroxyalkyl groups, thioalkyl groups, cyanoalkyl groups, alkoxy groups, acyl groups, acetyloxy groups, cycloalkyl groups, aryl groups, alkylaryl groups, and groups having the formula —NHR$_N$ wherein R$_N$ is chosen from a hydrogen atom, alkyl groups, monohydroxyalkyl groups, polyhydroxyalkyl groups, acetyl groups, and ureido groups; and R₄ and R₅ may optionally also form, together with the atoms to which they are attached, at least one 5- to 7-membered aromatic ring.

168. A process according to claim 167, wherein both of said A₁⁺ and said A₂⁺ are chosen from quaternary imidazole groups of formula (IV), wherein R₃, R₄, and R₅, which may be identical or different, are each chosen from a hydrogen atom, hydroxyl groups, nitro groups, cyano groups, mercapto groups, carboxyl groups, alkyl groups, monohydroxyalkyl groups, and polyhydroxyalkyl groups;

wherein said R₄ and R₅ may optionally also form, together with the atoms to which they are attached, at least one 5- to 7-membered aromatic ring.

169. A process according to claim 167, wherein both of said A₁₊ and said A₂⁺ are chosen from quaternary imidazole groups of formula (IV), wherein R₃, R₄, and R₅, which may be identical or different, are each chosen from a hydrogen atom, and C₁ to C₆ alkyl groups;

wherein said R₄ and R₅ may optionally also form, together with the atoms to which they are attached, at least one phenyl ring.

170. A process according to claim 166, wherein at least one of said A₁⁺ and said A₂⁺ is chosen from unsaturated quaternary heterocycles of formula (II), and wherein said unsaturated quaternary heterocycles of formula (II) are chosen from

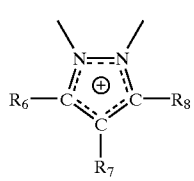

(V)

quaternary pyrazole groups of formula (V):

wherein:

R₆, R₇, and R₈, which may be identical or different, are each chosen from a hydrogen atom, halogen atoms, hydroxyl groups, nitro groups, cyano groups, mercapto groups, carboxyl groups, alkyl groups, monohydroxyalkyl groups, polyhydroxyalkyl groups, thioalkyl groups, cyanoalkyl groups, alkoxy groups, acyl groups, acetyloxy groups, cycloalkyl groups, aryl groups, alkylaryl groups, and groups having the formula —NHR$_N$, wherein R$_N$ is chosen from a hydrogen atom, alkyl groups, monohydroxyalkyl groups, polyhydroxyalkyl groups, acetyl groups, and ureido groups; and wherein two of said R₆, R₇, and R₈ may optionally also form, together with the atoms to which they are attached, at least one 5- to 7-membered aromatic ring.

171. A process according to claim 166, wherein said A₁⁺ is chosen from unsaturated quaternary heterocycles of formula (II), and wherein said unsaturated quaternary heterocycles of formula (II) are chosen from quaternary imidazole groups of formula (IV):

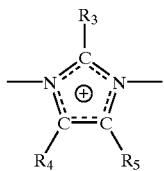

(IV)

wherein:

$R_3$, $R_4$, and $R_5$, which may be identical or different, are each chosen from a hydrogen atom, halogen atoms, hydroxyl groups, nitro groups, cyano groups, mercapto groups, carboxyl groups, alkyl groups, monohydroxyalkyl groups, polyhydroxyalkyl groups, thioalkyl groups, cyanoalkyl groups, alkoxy groups, acyl groups, acetyloxy groups, cycloalkyl groups, aryl groups, alkylaryl groups, and groups having the formula —$NHR_N$ wherein $R_N$ is chosen from a hydrogen atom, alkyl groups, monohydroxyalkyl groups, polyhydroxyalkyl groups, acetyl groups, and ureido groups; and $R_4$ and $R_5$ may optionally also form, together with the atoms to which they are attached, at least one 5- to 7-membered aromatic ring; and further wherein said $A_2^+$ is chosen from unsaturated quaternary heterocycles of formula (II), and wherein said unsaturated quaternary heterocycles of formula (II) are

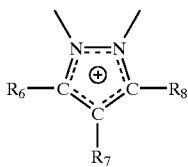

(V)

chosen from quaternary pyrazole groups of formula (V):
wherein:

$R_6$, $R_7$, and $R_8$, which may be identical or different, are each chosen from a hydrogen atom, halogen atoms, hydroxyl groups, nitro groups, cyano groups, mercapto groups, carboxyl groups, alkyl groups, monohydroxyalkyl groups, polyhydroxyalkyl groups, thioalkyl groups, cyanoalkyl groups, alkoxy groups, acyl groups, acetyloxy groups, cycloalkyl groups, aryl groups, alkylaryl groups, and groups having the formula —$NHR_N$, wherein $R_N$ is chosen from a hydrogen atom, alkyl groups, monohydroxyalkyl groups, polyhydroxyalkyl groups, acetyl groups, and ureido groups; and wherein two of said $R_6$, $R_7$, and $R_8$ may optionally also form, together with the atoms to which they are attached, at least one 5- to 7-membered aromatic ring.

172. A process according to claim 166, wherein said $A_1^+$ is chosen from quaternary ammoniums of formula (III), and wherein said $A_2^+$ is chosen from unsaturated quaternary heterocycles of formula (II), and wherein said unsaturated quaternary heterocycles of formula (II) are chosen from quaternary imidazole groups of formula (IV):

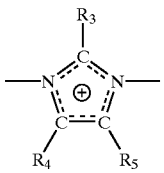

(IV)

wherein:

$R_3$, $R_4$, and $R_5$, which may be identical or different, are each chosen from a hydrogen atom, halogen atoms, hydroxyl groups, nitro groups, cyano groups, mercapto groups, carboxyl groups, alkyl groups, monohydroxyalkyl groups, polyhydroxyalkyl groups, thioalkyl groups, cyanoalkyl groups, alkoxy groups, acyl groups, acetyloxy groups, cycloalkyl groups, aryl groups, alkylaryl groups, and groups having the formula —$NHR_N$ wherein $R_N$ is chosen from a hydrogen atom, alkyl groups, monohydroxyalkyl groups, polyhydroxyalkyl groups, acetyl groups, and ureido groups; and $R_4$ and $R_5$ may optionally also form, together with the atoms to which they are attached, at least one 5- to 7-membered aromatic ring.

173. A process according to claim 166, wherein said $A_2^+$ is chosen from unsaturated quaternary heterocycles of formula (II), and wherein said unsaturated quaternary heterocycles of formula (II) are chosen from quaternary imidazole groups of formula (IV):

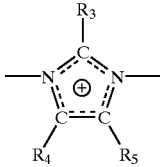

(IV)

wherein:

$R_4$ and $R_5$, which may be identical or different, are each chosen from a hydrogen atom, halogen atoms, hydroxyl groups, nitro groups, cyano groups, mercapto groups, carboxyl groups, alkyl groups, monohydroxyalkyl groups, polyhydroxyalkyl groups, thioalkyl groups, cyanoalkyl groups, alkoxy groups, acyl groups, acetyloxy groups, cycloalkyl groups, aryl groups, alkylaryl groups, groups having the formula —$NHR_N$ in which $R_N$ is chosen from a hydrogen atom, alkyl groups, monohydroxyalkyl groups, polyhydroxyalkyl groups, acetyl groups, and ureido groups; and $R_3$ is chosen from cycloalkyl groups, aryl groups, and alkylaryl groups.

174. A process according to claim 166, wherein at least one of said $B_1$ and $B_2$, which may be identical or different, is chosen from groups of formula (VI):

—$(CH_2)_n$—CO—A—OC—$(CH_2)_n$— (VI)

wherein:

n is an integer ranging from 1 to 10;

A is chosen from:

(a) glycol residues of formula: —O—Z—O— in which Z is chosen from hydrocarbons, and groups having the formula:

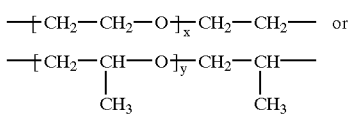

wherein x and y, which may be identical or different, are each a number ranging from 1 to 4;
(b) bis(secondary amine) groups;
(c) bis(primary amine) groups having the formula:

wherein Y is chosen from hydrocarbons, and groups having the formula —$(CH_2)_2$—S—S—$(CH_2)_2$—; and
(d) ureylene groups.

175. A process according to claim 174, wherein n is an integer from 1 to 6.

176. A process according to claim 166, wherein said $B_1$ and $B_2$, which may be identical or different, are each chosen from:
(a) groups having the formula:

wherein n is an integer ranging from 1 to 6;
(b) groups having the formula:

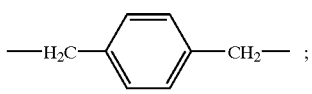

and
(c) groups having the formula:

177. A process according to claim 166, wherein said $X^-$ is chosen from halide anions.

178. A process according to claim 166, wherein said composition further comprises a medium appropriate for bleaching for eratinous fibers.

179. A process according to claim 178, wherein said at least one bleaching agent is chosen from hydrogen peroxide, persulphates, percarbonates, and perborates.

180. A process for protecting at least one keratinous fiber comprising applying to said at least one keratinous fiber an effective amount of at least one polymer comprising at least one unit of formula (I):

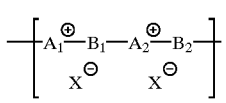

wherein:
$A_1^+$ and $A_2^+$, which may be identical or different, are each chosen from:

(a) unsaturated quaternary heterocycles of formula (II):

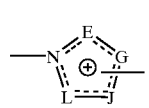

wherein:
E, G, L, and J, which may be identical or different, are each chosen from a carbon atom, an oxygen atom, a sulphur atom, and a nitrogen atom, wherein at least one of E, G, L, and J is a nitrogen atom;
and further wherein when at least one of E, G, L, and J is a carbon atom, said carbon atom may optionally be substituted by at least one substituent chosen from halogen atoms, hydroxyl groups, nitro groups, cyano groups, mercapto groups, carboxyl groups, alkyl groups, monohydroxyalkyl groups, polyhydroxyalkyl groups, thioalkyl groups, cyanoalkyl groups, alkoxy groups, acyl groups, acetyloxy groups, cycloalkyl groups, optionally substituted, aryl groups, optionally substituted, alkylaryl groups, optionally substituted, and groups having the formula —$NHR_N$ wherein $R_N$ is chosen from a hydrogen atom, alkyl groups, monohydroxyalkyl groups, polyhydroxyalkyl groups, acetyl groups, and ureido groups;
with the proviso that when at least two of said E, G, L, and J are each nitrogen atoms, then at least one of said at least two of said E, G, L, and J may be substituted with a substituent chosen from a hydrogen atom, alkyl groups, monohydroxyalkyl groups, polyhydroxyalkyl groups, aryl groups, optionally substituted, and alkylaryl groups, optionally substituted;
with the further proviso that when at least two of E, G, L, and J are substituted, the substituents may optionally also form, together with the atoms to which they are attached, at least one 5- to 7-membered aromatic ring, optionally substituted; and (b) quaternary ammoniums of formula (III):

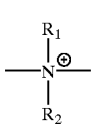

wherein:
$R_1$ and $R_2$, which may be identical or different, are each chosen from carboxyl groups, alkyl groups, polyhydroxyalkyl groups, thioalkyl groups, cyanoalkyl groups, alkoxy groups, acyl groups, acetyloxy groups, cycloalkyl groups, optionally substituted, aryl groups, optionally substituted, alkylaryl groups, optionally substituted, and groups having the formula —$NHR_N$ wherein $R_N$ is chosen from a hydrogen atom, alkyl groups, monohydroxyalkyl groups, polyhydroxyalkyl groups, acetyl groups, and ureidogroups;
wherein $R_1$ and $R_2$ may optionally also form, together with the nitrogen atom to which they are attached, at least one saturated 5- to 7-membered carbon-based ring;

with the proviso that at least one of said $A_1^+$ and said $A_2^+$ is chosen from said unsaturated quaternary heterocycles of formula (II);

$B_1$ and $B_2$, which may be identical or different, are each chosen from hydrocarbons optionally having at least one substituent chosen from optionally substituted aromatic rings, an oxygen atom, a sulphur atom, a nitrogen atom, an —SO— group, an —SO$_2$— group, an —SO$_3$H group, amino groups, alkylamino groups, hydroxyl groups, quaternary ammonium groups, and ureido groups wherein said at least one substituent is bonded to or inserted in the main chain of said polymer; and $X^-$ is chosen from halide anions and anions derived from at least one acid chosen from organic acids and inorganic acids.

181. A process according to claim 180, wherein at least one of said $A_1^+$ and said $A_2^+$ is chosen from unsaturated quaternary heterocycles of formula (II), and wherein said unsaturated quaternary heterocycles of formula (II) are chosen from quaternary imidazole groups of formula (IV):

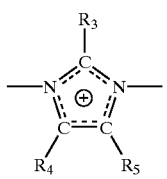

(IV)

wherein:

$R_3$, $R_4$, and $R_5$, which may be identical or different, are each chosen from a hydrogen atom, halogen atoms, hydroxyl groups, nitro groups, cyano groups, mercapto groups, carboxyl groups, alkyl groups, monohydroxyalkyl groups, polyhydroxyalkyl groups, thioalkyl groups, cyanoalkyl groups, alkoxy groups, acyl groups, acetyloxy groups, cycloalkyl groups, aryl groups, alkylaryl groups, and groups having the formula —NHR$_N$, wherein $R_N$ is chosen from a hydrogen atom, alkyl groups, monohydroxyalkyl groups, polyhydroxyalkyl groups, acetyl groups, and ureido groups; and $R_4$ and $R_5$ may optionally also form, together with the atoms to which they are attached, at least one 5- to 7-membered arornqtic ring.

182. A process according to claim 181, wherein both of said $A_1^+$ and said $A_2^+$ are chosen from quaternary imidazole groups of formula (IV), wherein $R_3$, $R_4$, and $R_5$, which may be identical or different, are each chosen from a hydrogen atom, hydroxyl groups, nitro groups, cyano groups, mercapto groups, carboxyl groups, alkyl groups, monohydroxyalkyl groups, and polyhydroxyalkyl groups;

wherein said $R_4$ and $R_5$ may optionally also form, together with the atoms to which they are attached, at least one 5- to 7-membered aromatic ring.

183. A process according to claim 181, wherein both of said $A_1^+$ and said $A_2^+$ are chosen from quaternary imidazole groups of formula (IV), wherein $R_3$, $R_4$, and $R_5$, which may be identical or different, are each chosen from a hydrogen atom, and $C_1$ to $C_6$ alkyl groups;

wherein said $R_4$ and $R_5$ may optionally also form, together with the atoms to which they are attached, at least one phenyl ring.

184. A process according to claim 180, wherein at least one of said $A_1^+$ and said $A_2^+$ is chosen from unsaturated quaternary heterocycles of formula (II), and wherein said unsaturated quaternary heterocycles of formula (II) are chosen from quaternary pyrazole groups of formula (V):

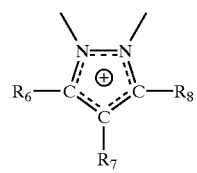

(V)

wherein:

$R_6$, $R_7$, and $R_8$, which may be identical or different, are each chosen from a hydrogen atom, halogen atoms, hydroxyl groups, nitro groups, cyano groups, mercapto groups, carboxyl groups, alkyl groups, monohydroxyalkyl groups, polyhydroxyalkyl groups, thioalkyl groups, cyanoalkyl groups, alkoxy groups, acyl groups, acetyloxy groups, cycloalkyl groups, aryl groups, alkylaryl groups, and groups having the formula —NHR$_N$, wherein $R_N$ is chosen from a hydrogen atom, alkyl groups, monohydroxyalkyl groups, polyhydroxyalkyl groups, acetyl groups, and ureido groups; and wherein two of said $R_6$, $R_7$, and $R_8$ may optionally also form, together with the atoms to which they are attached, at least one 5- to 7-membered aromatic ring.

185. A process according to claim 180, wherein said $A_1^+$ is chosen from unsaturated quaternary heterocycles of formula (II), and wherein said unsaturated quaternary heterocycles of formula (II) are chosen from quaternary imidazole groups of formula (IV):

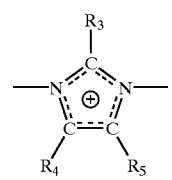

(IV)

wherein:

$R_3$, $R_4$, and $R_5$, which may be identical or different, are each chosen from a hydrogen atom, halogen atoms, hydroxyl groups, nitro groups, cyano groups, mercapto groups, carboxyl groups, alkyl groups, monohydroxyalkyl groups, polyhydroxyalkyl groups, thioalkyl groups, cyanoalkyl groups, alkoxy groups, acyl groups, acetyloxy groups, cycloalkyl groups, aryl groups, alkylaryl groups, and groups having the formula —NHR$_N$ wherein $R_N$ is chosen from a hydrogen atom, alkyl groups, monohydroxyalkyl groups, polyhydroxyalkyl groups, acetyl groups, and ureido groups; and $R_4$ and $R_5$ may optionally also form, together with the atoms to which they are attached, at least one 5- to 7-membered aromatic ring; and further wherein said $A_2^+$ is chosen from unsaturated quaternary heterocycles of formula (II), and wherein said unsaturated quaternary heterocycles of formula (II) are chosen from quaternary pyrazole groups of formula (V):

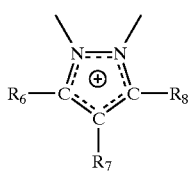

(V)

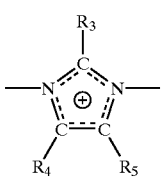

(IV)

wherein:

$R_6$, $R_7$, and $R_8$, which may be identical or different, are each chosen from a hydrogen atom, halogen atoms, hydroxyl groups, nitro groups, cyano groups, mercapto groups, carboxyl groups, alkyl groups, monohydroxyalkyl groups, polyhydroxyalkyl groups, thioalkyl groups, cyanoalkyl groups, alkoxy groups, acyl groups, acetyloxy groups, cycloalkyl groups, aryl groups, alkylaryl groups, and groups having the formula —$NHR_N$, wherein $R_N$ is chosen from a hydrogen atom, alkyl groups, monohydroxyalkyl groups, polyhydroxyalkyl groups, acetyl groups, and ureido groups; and wherein two of said $R_6$, $R_7$, and $R_8$ may optionally also form, together with the atoms to which they are attached, at least one 5- to 7-membered aromatic ring.

186. A process according to claim 180, wherein said $A_1^+$ is chosen from quaternary ammoniums of formula (III), and wherein said $A_2^+$ is chosen from unsaturated quaternary heterocycles of formula (II), and wherein said unsaturated quaternary heterocycles of formula (II) are chosen from quaternary imidazole groups of formula (IV):

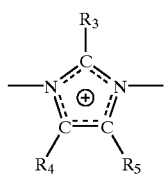

(IV)

wherein:

$R_3$, $R_4$, and $R_5$, which may be identical or different, are each chosen from a hydrogen atom, halogen atoms, hydroxyl groups, nitro groups, cyano groups, mercapto groups, carboxyl groups, alkyl groups, monohydroxyalkyl groups, polyhydroxyalkyl groups, thioalkyl groups, cyanoalkyl groups, alkoxy groups, acyl groups, acetyloxy groups, cycloalkyl groups, aryl groups, alkylaryl groups, and groups having the formula —$NHR_N$, wherein $R_N$ is chosen from a hydrogen atom, alkyl groups, monohydroxyalkyl groups, polyhydroxyalkyl groups, acetyl groups, and ureido groups; and $R_4$ and $R_5$ may optionally also form, together with the atoms to which they are attached, at least one 5- to 7-membered aromatic ring.

187. A process according to claim 180, wherein said $A_2^+$ is chosen from unsaturated quaternary heterocycles of formula (II), and wherein said unsaturated quaternary heterocycles of formula (II) are chosen from quaternary imidazole groups of formula (IV):

wherein:

$R_4$ and $R_5$, which may be identical or different, are each chosen from a hydrogen atom, halogen atoms, hydroxyl groups, nitro groups, cyano groups, mercapto groups, carboxyl groups, alkyl groups, monohydroxyalkyl groups, polyhydroxyalkyl groups, thioalkyl groups, cyanoalkyl groups, alkoxy groups, acyl groups, acetyloxy groups, cycloalkyl groups, aryl groups, alkylaryl groups, groups having the formula —$NHR_N$ in which $R_N$ is chosen from a hydrogen atom, alkyl groups, monohydroxyalkyl groups, polyhydroxyalkyl groups, acetyl groups, and ureido groups; and $R_3$ is chosen from cycloalkyl groups, aryl groups, and alkylaryl groups.

188. A process according to claim 180, wherein at least one of said $B_1$ and $B_2$, which may be identical or different, is chosen from groups of formula (VI):

—$(CH_2)_n$—CO—A—OC—$(CH_2)_n$—  (VI)

wherein:

n is an integer ranging from 1 to 10;

A is chosen from:

(a) glycol residues of formula: —O—Z—O— in which Z is chosen from hydrocarbons, and groups having the formula:

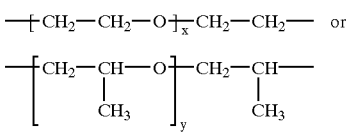

wherein x and y, which may be identical or different, are each a number ranging from 1 to 4;

(b) bis(secondary amine) groups;

(c) bis(primary amine) groups having the formula:

—NH—Y—NH— wherein Y is chosen from hydrocarbons, and groups having the formula —$(CH_2)_2$—S—S—$(CH_2)_2$—; and (d) ureylene groups.

189. A process according to claim 188, wherein n is an integer from 1 to 6.

190. A process according to claim 180, wherein said $B_1$ and $B_2$, which may be identical or different, are each chosen from:

(a) groups having the formula:

—$(CH_2)_n$— wherein n is an integer ranging from 1 to 6;

(b) groups having the formula:

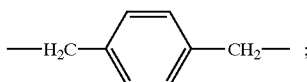

and (c) groups having the formula:

191. A process according to claim 180, wherein said $X^-$ is chosen from halide anions.

192. A process for permanent shaping of at least one keratinous fiber comprising:
(a) applying an effective amount of a reducing composition to said at least one keratinous fiber;
(b) applying an effective amount of an oxidizing composition after a sufficient time to reduce keratin in said at least one keratinous fiber; and
(c) rinsing said at least one keratinous fiber after a sufficient time to fix said at least one keratinous fiber in a permanent shape;
wherein said reducing composition comprises:
(i) at least one reducing agent; and
(ii) at least one polymer comprising at least one unit of formula (I):

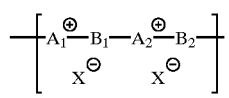

wherein:
$A_1^+$ and $A_2^+$, which may be identical or different, are each chosen from:
(a) unsaturated quaternary heterocycles of formula (II):

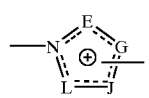

wherein:
E, G, L, and J, which may be identical or different, are each chosen from a carbon atom, an oxygen atom, a sulphur atom, and a nitrogen atom,
wherein at least one of E, G, L, and J is a nitrogen atom;
and further wherein when at least one of E, G, L, and J is a carbon atom, said carbon atom may optionally be substituted by at least one substituent chosen from halogen atoms, hydroxyl groups, nitro groups, cyano groups, mercapto groups, carboxyl groups, alkyl groups, monohydroxyalkyl groups, polyhydroxyalkyl groups, thioalkyl groups, cyanoalkyl groups, alkoxy groups, acyl groups, acetyloxy groups, cycloalkyl groups, optionally substituted, aryl groups, optionally substituted, alkylaryl groups, optionally substituted, and groups having the formula —$NHR_N$ wherein $R_N$ is chosen from a hydrogen atom, alkyl groups, monohydroxyalkyl groups, polyhydroxyalkyl groups, acetyl groups, and ureido groups;
with the proviso that when at least two of said E, G, L, and J are each nitrogen atoms, then at least one of said at least two of said E, G, L, and J may be substituted with a substituent chosen from a hydrogen atom, alkyl groups, monohydroxyalkyl groups, polyhydroxyalkyl groups, aryl groups, optionally substituted, and alkylaryl groups, optionally substituted;
with the further proviso that when at least two of E, G, L, and J are substituted, the substituents may optionally also form, together with the atoms to which they are attached, at least one 5- to 7-membered aromatic ring, optionally substituted; and
(b) quaternary ammoniums of formula (III):

wherein:
$R_1$ and $R_2$, which may be identical or different, are each chosen from carboxyl groups, alkyl groups, polyhydroxyalkyl groups, thioalkyl groups, cyanoalkyl groups, alkoxy groups, acyl groups, acetyloxy groups, cycloalkyl groups, optionally substituted, aryl groups, optionally substituted, alkylaryl groups, optionally substituted, and groups having the formula —$NHR_N$ wherein $R_N$ is chosen from a hydrogen atom, alkyl groups, monohydroxyalkyl groups, polyhydroxyalkyl groups, acetyl groups, and ureido groups;
wherein $R_1$ and $R_2$ may optionally also form, together with the nitrogen atom to which they are attached, at least one saturated 5- to 7-membered carbon-based ring;
with the proviso that at least one of said $A_1^+$ and said $A_2^+$ is chosen from said unsaturated quaternary heterocycles of formula (II);
$B_1$ and $B_2$, which may be identical or different, are each chosen from hydrocarbons optionally having at least one substituent chosen from optionally substituted aromatic rings, an oxygen atom, a sulphur atom, a nitrogen atom, an —SO— group, an —$SO_2$— group, an —$SO_3H$ group, amino groups, alkylamino groups, hydroxyl groups, quaternary ammonium groups, and ureido groups wherein said at least one substituent is bonded to or inserted in the main chain of said polymer; and
$X^-$ is chosen from halide anions and anions derived from at least one acid chosen from organic acids and inorganic acids; and
wherein said oxidizing composition comprises:
(a) at least one oxidizing agent; and
(b) at least one polymer comprising at least one unit of formula (I) as defined above, which may be identical to, or different from, said at least one polymer comprising at least one unit of formula (I) in said reducing composition.

193. A process according to claim 192, wherein at least one of said $A_1^+$ and said $A_2^+$ is chosen from unsaturated quaternary heterocycles of formula (II), and wherein said unsaturated quaternary heterocycles of formula (II) are chosen from quaternary imidazole groups of formula (IV):

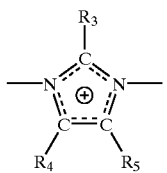

(IV)

wherein:

$R_3$, $R_4$, and $R_5$, which may be identical or different, are each chosen from a hydrogen atom, halogen atoms, hydroxyl groups, nitro groups, cyano groups, mercapto groups, carboxyl groups, alkyl groups, monohydroxyalkyl groups, polyhydroxyalkyl groups, thioalkyl groups, cyanoalkyl groups, alkoxy groups, acyl groups, acetyloxy groups, cycloalkyl groups, aryl groups, alkylaryl groups, and groups having the formula —$NHR_N$, wherein $R_N$ is chosen from a hydrogen atom, alkyl groups, monohydroxyalkyl groups, polyhydroxyalkyl groups, acetyl groups, and ureido groups; and $R_4$ and $R_5$ may optionally also form, together with the atoms to which they are attached, at least one 5- to 7-membered aromatic ring.

194. A process according to claim 193, wherein both of said $A_1^+$ and said $A_2^+$ are chosen from quaternary imidazole groups of formula (IV), wherein $R_3$, $R_4$, and $R_5$, which may be identical or different, are each chosen from a hydrogen atom, hydroxyl groups, nitro groups, cyano groups, mercapto groups, carboxyl groups, alkyl groups, monohydroxyalkyl groups, and polyhydroxyalkyl groups;

wherein said $R_4$ and $R_5$ may optionally also form, together with the atoms to which they are attached, at least one 5- to 7-membered aromatic ring.

195. A process according to claim 193, wherein both of said $A_1^+$ and said $A_2^+$ are chosen from quaternary imidazole groups of formula (IV), wherein $R_3$, $R_4$, and $R_5$, which may be identical or different, are each chosen from a hydrogen atom, and $C_1$ to $C_6$ alkyl groups;

wherein said $R_4$ and $R_5$ may optionally also form, together with the atoms to which they areattached, at least one phenyl ring.

196. A process according to claim 192, wherein at least one of said $A_1^+$ and said $A_2^+$ is chosen from unsaturated quaternary heterocycles of formula (II), and wherein said unsaturated quaternary heterocycles of formula (II) are chosen from quaternary pyrazole groups of formula (V):

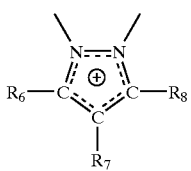

(V)

wherein:

$R_6$, $R_7$, and $R_8$, which may be identical or different, are each chosen from a hydrogen atom, halogen atoms, hydroxyl groups, nitro groups, cyano groups, mercapto groups, carboxyl groups, alkyl groups, monohydroxyalkyl groups, polyhydroxyalkyl groups, thioalkyl groups, cyanoalkyl groups, alkoxy groups, acyl groups, acetyloxy groups, cycloalkyl groups, aryl groups, alkylaryl groups, and groups having the formula —$NHR_N$, wherein $R_N$ is chosen from a hydrogen atom, alkyl groups, monohydroxyalkyl groups, polyhydroxyalkyl groups, acetyl groups, and ureido groups; and wherein two of said $R_6$, $R_7$, and $R_8$ may optionally also form, together with the atoms to which they are attached, at least one 5- to 7-membered aromatic ring.

197. A process according to claim 192, wherein said $A_1^+$ is chosen from unsaturated quaternary heterocycles of formula (II), and wherein said unsaturated quaternary heterocycles of formula (II) are chosen from quaternary imidazole groups of formula (IV):

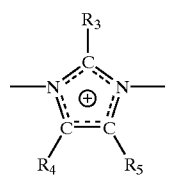

(IV)

wherein:

$R_3$, $R_4$, and $R_5$, which may be identical or different, are each chosen from a hydrogen atom, halogen atoms, hydroxyl groups, nitro groups, cyano groups, mercapto groups, carboxyl groups, alkyl groups, monohydroxyalkyl groups, polyhydroxyalkyl groups, thioalkyl groups, cyanoalkyl groups, alkoxy groups, acyl groups, acetyloxy groups, cycloalkyl groups, aryl groups, alkylaryl groups, and groups having the formula —$NHR_N$, wherein $R_N$ is chosen from a hydrogen atom, alkyl groups, monohydroxyalkyl groups, polyhydroxyalkyl groups, acetyl groups, and ureido groups; and $R_4$ and $R_5$ may optionally also form, together with the atoms to which they are attached, at least one 5- to 7-membered aromatic ring; and further wherein said $A_2^+$ is chosen from unsaturated quaternary heterocycles of formula (II), and wherein said unsaturated quaternary heterocycles of formula (II) are chosen from quaternary pyrazole groups of formula (V):

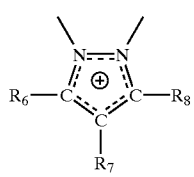

(V)

wherein:

$R_6$, $R_7$, and $R_8$, which may be identical or different, are each chosen from a hydrogen atom, halogen atoms, hydroxyl groups, nitro groups, cyano groups, mercapto groups, carboxyl groups, alkyl groups, monohydroxyalkyl groups, polyhydroxyalkyl groups, thioalkyl groups, cyanoalkyl groups, alkoxy groups, acyl groups, acetyloxy groups, cycloalkyl groups, aryl groups, alkylaryl groups, and groups having the formula —$NHR_N$, wherein $R_N$ is chosen from a hydrogen atom, alkyl groups, monohydroxyalkyl groups, polyhydroxyalkyl groups, acetyl groups, and ureido groups; and wherein two of said $R_6$, $R_7$, and $R_8$ may optionally also form, together with the atoms to which they are attached, at least one 5- to 7-membered aromatic ring.

198. A process according to claim 192, wherein said $A_1^+$ is chosen from quaternary ammoniums of formula (III), and wherein said $A_2^+$ is chosen from unsaturated quaternary heterocycles of formula (II), and wherein said unsaturated quaternary heterocycles of formula (II) are chosen from quaternary imidazole groups of formula (IV):

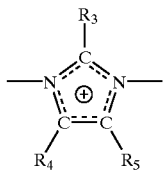

(IV)

wherein:

$R_3$, $R_4$, and $R_5$, which may be identical or different, are each chosen from a hydrogen atom, halogen atoms, hydroxyl groups, nitro groups, cyano groups, mercapto groups, carboxyl groups, alkyl groups, monohydroxyalkyl groups, polyhydroxyalkyl groups, thioalkyl groups, cyanoalkyl groups, alkoxy groups, acyl groups, acetyloxy groups, cycloalkyl groups, aryl groups, alkylaryl groups, and groups having the formula —$NHR_N$ wherein $R_N$ is chosen from a hydrogen atom, alkyl groups, monohydroxyalkyl groups, polyhydroxyalkyl groups, acetyl groups, and ureido groups; and $R_4$ and $R_5$ may optionally also form, together with the atoms to which they are attached, at least one 5- to 7-membered aromatic ring.

199. A process according to claim 192, wherein said $A_2^+$ is chosen from unsaturated quaternary heterocycles of formula (II), and wherein said unsaturated quaternary heterocycles of formula (II) are chosen from quaternary imidazole groups of formula (IV):

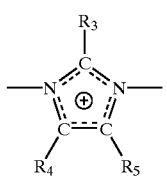

(IV)

wherein:

$R_4$ and $R_5$, which may be identical or different, are each chosen from a hydrogen atom, halogen atoms, hydroxyl groups, nitro groups, cyano groups, mercapto groups, carboxyl groups, alkyl groups, monohydroxyalkyl groups, polyhydroxyalkyl groups, thioalkyl groups, cyanoalkyl groups, alkoxy groups, acyl groups, acetyloxy groups, cycloalkyl groups, aryl groups, alkylaryl groups, groups having the formula —$NHR_N$ in which $R_N$ is chosen from a hydrogen atom, alkyl groups, monohydroxyalkyl groups, polyhydroxyalkyl groups, acetyl groups, and ureido groups; and $R_3$ is chosen from cycloalkyl groups, aryl groups, and alkylaryl groups.

200. A process according to claim 192, wherein at least one of said $B_1$ and $B_2$, which may be identical or different, is chosen from groups of formula (VI):

—$(CH_2)_n$—CO—A—OC—$(CH_2)_n$— (VI)

wherein:

n is an integer ranging from 1 to 10;

A is chosen from:

(a) glycol residues of formula: —O—Z—O— in which Z is chosen from hydrocarbons, and groups having the formula:

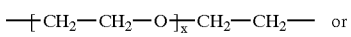

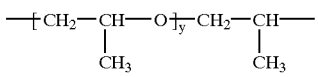

wherein x and y, which may be identical or different, are each a number ranging from 1 to 4;

(b) bis(secondary amine) groups;
(c) bis(primary amine) groups having the formula:

—NH—Y—NH— wherein Y is chosen from hydrocarbons, and groups having the formula —$(CH_2)_2$—S—S—$(CH_2)_2$—; and (d) ureylene groups.

201. A process according to claim 200, wherein n is an integer from 1 to 6.

202. A process according to claim 192, wherein said $B_1$ and $B_2$, which may be identical or different, are each chosen from:

(a) groups having the formula:

—$(CH_2)_n$— wherein n is an integer ranging from 1 to 6;

(b) groups having the formula:

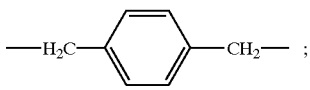

and (c) groups having the formula:

—$(CH_2)_2$—O—$(CH_2)_2$—O—$(CH_2)_2$—.

203. A process according to claim 192, wherein said $X^-$ is chosen from halide anions.

204. A process according to claim 192, wherein said at least one reducing agent is chosen from sulphites, bisulphites, and thiols.

205. A process according to claim 204, wherein said at least one reducing agent is chosen from cysteine, cysteamine, and thiolactic acid, and thioglycolic acid.

206. A process according to claim 205, wherein said derivatives of at least one reducing agent are chosen from salts of at least one reducing agent.

207. A process according to claim 206, wherein said salts are acid addition salts.

208. A process according to claim 207, wherein said acid addition salts are chosen from hydrochlorides, hydrobromides, citrates, acetates, sulphates, and thiolactates.

209. A process according to claim 192, wherein said at least one polymer comprising at least one unit of formula (I) is present in said reducing composition in an amount ranging from 0.01% to 10% by weight, relative to the total weight of said reducing composition.

210. A process according to claim 209, wherein said at least one polymer comprising at least one unit of formula (I) is present in said reducing composition in an amount ranging from 1% to 5% by weight, relative to the total weight of said composition.

211. A process according to claim 192, wherein said at least one reducing agent is present in said reducing composition in an amount ranging from 1% to 25% by weight, relative to the total weight of said reducing composition.

212. A process according to claim 211, wherein said at least one reducing agent is present in said reducing composition in an amount ranging from 1% to 10% by weight, relative to the total weight of said reducing composition.

213. A process according to claim 192, wherein said reducing composition has a pH ranging from 6.5 to 11.5.

214. A process according to claim 192, wherein said reducing composition further comprises at least one surface active agent chosen from nonionic surface active agents, anionic surface active agents, cationic surface active agents, and amphoteric surface active agents.

215. A process according to claim 214, wherein said at least one surface active agent is chosen from alkyl sulphates, alkylbenzenesulphonates, alkyl ether suiphates, alkylsulphonates, quaternary ammonium salts, alkyl betaines, oxyethylenated alkylphenols, alkylpolyglucosides, fatty acid alkanolamides, oxyethylenated fatty acid esters, and hydroxypropyl ethers.

216. A process according to claim 214, wherein said at least one surface active agent is present in said reducing composition in an amount up to 30% by weight, relative to the total weight of said reducing composition.

217. A process according to claim 216, wherein said at least one surface active agent is present in said reducing composition in an amount ranging from 0.5% to 10% by weight, relative to the total weight of said reducing composition.

218. A process according to claim 214, wherein said reducing composition further comprises at least one additive chosen from thickening agents, treating agents, waxes, anionic polymers, cationic polymers different from said at least one polymer as defined in claim 34, nonionic polymers, amphoteric polymers, swelling agents, penetrating agents, fatty alcohols, lanolins, ceramides, active ingredients, agents for combating hair loss, antidandruff agents, suspending agents, sequestering agents, opacifying agents, dyes, silicone-comprising and non-silicone-comprising sunscreens, fragrances, and preservatives.

219. A process according to claim 218, wherein said thickening agents are chosen from guar gums, tara gums, and spruce flours.

220. A process according to claim 218, wherein said treating agents are chosen from volatile and non-volatile, linear, branched, and cyclic silicones.

221. A process according to claim 220, wherein said silicones are chosen from polydimethylsiloxanes, quaternized polyorganosiloxanes, polyorganosiloxanes comprising at least one aminoalkyl group, optionally modified by alkoxycarbonylalkyl groups, and polyorganosiloxanes.

222. A process according to claim 221, wherein said polyorganosiloxanes are chosen from polydimethylsiloxane-polyoxyalkyl copolymers, polydimethylsiloxanes comprising end stearoxy groups, polydimethylsiloxane-dialkylammonium acetate copolymers, polydimethylsiloxane-poly(alkyl betaine) copolymers, polysiloxanes organomodified by mercapto groups, polysiloxanes organomodified by mercaptoalkyl groups, and silanes.

223. A process according to claim 222, wherein said silanes are chosen from stearoxytrimethylsilanes.

224. A process according to claim 218, wherein said ceramide derivatives are chosen from glycoceramides, and pseudoceramides.

225. A process according to claim 218, wherein said active ingredients are chosen from pantothenic acid and panthenol.

226. A process according to claim 218, wherein said swelling agents and penetrating agents are chosen from dimethylisosorbitol, urea, ureas, pyrrolidone, n-alkylpyrrolidone, thiamorpholinone, alkylene glycol alkyl ether, dialkylene glycol alkyl ether, $C_3$–$C_6$ alkanediols, and 2-imidazolidinone.

227. A process according to claim 226, wherein said glycol alkyl ethers are chosen from propylene glycol monomethyl ether and dipropylene glycol monomethyl ether.

228. A process according to claim 192, wherein said at least one oxidizing agent is chosen from aqueous hydrogen peroxide solution, urea hydrogen peroxide, bromates, persalts, and enzymes.

229. A process according to claim 228, wherein said bromates are chosen from alkaline bromates.

230. A process according to claim 228, wherein said enzymes are chosen from peroxidases, and two-electron oxidoreductases.

* * * * *

UNITED STATES PATENT AND TRADEMARK OFFICE
CERTIFICATE OF CORRECTION

PATENT NO. : 6,416,770 B1
DATED : July 9, 2002
INVENTOR(S) : Madeleine Leduc et al.

It is certified that error appears in the above-identified patent and that said Letters Patent is hereby corrected as shown below:

Column 31,
Line 37, "claim 50," should read -- claim 51, --.
Line 40, "pblymethylene" should read -- polymethylene --.

Column 36,
Line 25, "aromiatic" should read -- aromatic --.

Column 37,
Line 51, after "cysteamine,", delete "and".
Line 52, after "thiolactic acid,", insert -- and --.

Column 38,
Line 11, "claim 86," should read -- claim 85, --.
Lines 22-23, "claim 39," should read -- claim 4, --.

Column 40,
Line 23, "claim 103, herein" should read -- claim 102, wherein --.
Lines 28-29, "1,4-bis-N,N'-[(β,y-dihydroxypropyl)amino]-anthraquinone;" should read -- 1,4-bis-N,N'-[(β,γ-dihydroxypropyl)amino]-anthraquinone; --.
Lines 36-37, "1-methylamino-2-nitro-5-(β,y-dihydroxypropyloxy)benzene;" should read -- l-methylamino-2-nitro-5-(β,γ-dihydroxypropyloxy)benzene; --.

Column 46,
Line 59, "claim 123," should read -- claim 133, --.

Column 47,
Line 55, "claim 145," should read -- claim 148, --.

UNITED STATES PATENT AND TRADEMARK OFFICE
CERTIFICATE OF CORRECTION

PATENT NO. : 6,416,770 B1
DATED : July 9, 2002
INVENTOR(S) : Madeleine Leduc et al.

It is certified that error appears in the above-identified patent and that said Letters Patent is hereby corrected as shown below:

Column 48,
Line 3, "claim 152," should read -- claim 153, --.

Column 49,
Line 24, "$R_l$ is chosen" should read -- $R_{11}$ is chosen --.

Column 49,
Lines 38-39, "1,4-bis-N,N'-[(β,y-dihydroxypropyl)amino]-anthraquinone;" should read -- 1,4-bis-N,N'-[(β,γ-dihydroxypropyl)amino]-anthraquinone; --.
Lines 47-48, "1-methylamino-2-nitro-5-(β,y-dihydroxypropyloxy)benzene;" should read -- 1-methylamino-2-nitro-5-(β,γ-dihydroxypropyloxy)benzene; --.

Column 52,
Line 25, "said $A_{1+}$" should read -- said $A_1^+$ --.

Column. 55,
Line 48, "eratinous" should read -- keratinous --.

Column 56,
Line 63, "ureidogroups;" should read -- ureido groups; --.

Column 57,
Line 46, "arornqtic" should read -- aromatic --.

Column 60,
Line 30, "$-(CH_2)_n-CO-A-OC-(CH_2)_n-(VI)$" should read
-- $-(CH_2)_n-CO-A-OC-(CH_2)_n-$   (VI) --.

UNITED STATES PATENT AND TRADEMARK OFFICE
CERTIFICATE OF CORRECTION

PATENT NO.   : 6,416,770 B1
DATED        : July 9, 2002
INVENTOR(S)  : Madeleine et Leduc al.

It is certified that error appears in the above-identified patent and that said Letters Patent is hereby corrected as shown below:

Column 63,
Line 44, "areattached," should read -- are attached, --.

Column 66,
Line 48, after "cysteamine,", delete "and".

Column 67,
Line 18, "suiphates," should read -- sulphates, --.

Signed and Sealed this

Twenty-fourth Day of December, 2002

JAMES E. ROGAN
*Director of the United States Patent and Trademark Office*